United States Patent
Karger et al.

(10) Patent No.: US 6,674,070 B2
(45) Date of Patent: *Jan. 6, 2004

(54) ON-LINE AND OFF-LINE DEPOSITION OF LIQUID SAMPLES FOR MATRIX ASSISTED LASER DESORPTION IONIZATION-TIME OF FLIGHT (MALDI-TOF) MASS SPECTROSCOPY

(75) Inventors: Barry L. Karger, Newton, MA (US); Frantisek Foret, Malden, MA (US); Jan Preisler, Malden, MA (US)

(73) Assignee: Northeastern University, Boston, MA (US)

( * ) Notice: Subject to any disclaimer, the term of this patent is extended or adjusted under 35 U.S.C. 154(b) by 417 days.

This patent is subject to a terminal disclaimer.

(21) Appl. No.: 09/757,079
(22) Filed: Jan. 9, 2001
(65) Prior Publication Data

US 2001/0033809 A1 Oct. 25, 2001

Related U.S. Application Data

(63) Continuation-in-part of application No. 09/083,815, filed on May 22, 1998, now Pat. No. 6,175,112.
(60) Provisional application No. 60/047,489, filed on May 23, 1997.
(51) Int. Cl.[7] .......................... H01J 49/00; H01J 49/04
(52) U.S. Cl. ...................... 250/288; 250/281; 250/282; 250/287
(58) Field of Search ........................... 290/288, 281, 290/282, 287

(56) References Cited

U.S. PATENT DOCUMENTS

| | | | |
|---|---|---|---|
| 4,843,243 A | 6/1989 | Biemann et al. | 250/341 |
| 4,867,947 A | 9/1989 | Andresen et al. | 422/70 |

(List continued on next page.)

FOREIGN PATENT DOCUMENTS

| | | | |
|---|---|---|---|
| JP | 62296491 | 11/1987 | H01J/49/04 |
| WO | WO 97/26072 | 7/1997 | B01D/59/44 |

OTHER PUBLICATIONS

Kresbach et al., "Direct Electrically Heated Spray Device for a Moving Belt Liquid Chromatography–Mass Spectrometry Interface," J. Chrom. 394:89–100 (1987).

(List continued on next page.)

*Primary Examiner*—Nikita Wells
(74) *Attorney, Agent, or Firm*—Weingarten, Schurgin, Gagnebin & Lebovici LLP

(57) ABSTRACT

A universal interface for continuous on-line liquid sample introduction directly to the time-of-flight mass spectrometer, which can further promote throughput and utility of MALDI-TOF MS, is disclosed. Preferably, the liquid sample includes a matrix, either solid or liquid, for use in matrix-assisted-laser-desorption-ionization, most particularly in a time-of-flight mass spectrometer which can further promote throughput and utility of MALDI-TOF MS. In the method of the invention, the same samples and matrices, both solid and liquid, can be used as in conventional MALDI. In practice of the method of the invention, a solution of sample containing, e.g., peptide and matrix is infused directly into the source chamber of a mass spectrometer at subatmospheric pressure, deposited on a moving sample holder, such as a rotating quartz wheel, and desorbed by, e.g., a nitrogen laser. The method of the invention is particularly amenable to multiplexing, the parallel deposition of multiple samples, e.g., from a capillary array or microchip channels, with subsequent sequential desorption with a scanning laser. This format is particularly useful for high throughput MS analysis. Also disclosed is an off-line deposition chamber and a general method of preparing a sample for analysis that results in the homogeneous deposition of small quantities of sample at improved reproducibility. This format of sample preparation is particularly useful with existing commercial mass spectrometers.

27 Claims, 17 Drawing Sheets

U.S. PATENT DOCUMENTS

| | | | | |
|---|---|---|---|---|
| 5,382,793 | A | 1/1995 | Weinberger et al. | 250/288 |
| 5,770,860 | A | 6/1998 | Franzen | 250/288 |
| 5,841,136 | A | 11/1998 | Holle et al. | 250/288 |
| 6,175,112 | B1 * | 1/2001 | Karger et al. | 250/288 |

OTHER PUBLICATIONS

Ling He et al., "Continuos–Flow MALDI Mass Spectrometry Using an Ion Trap/Reflection Time–of–flight Detector," 67:2251–2257 (1997).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet," Anal. Chem. 69:4540–4546 (1997).

Allmaier et al., "Letter to the Editor," Rapid Commun. Mass Spec. 11:1567–1169 (1997).

Allwood et al., "Preparation of "Near" Homogeneous Samples for the Analysis of Matrix–Assisted Laser Desorption/Ionization Processes," Appl. Surface Sci. 103:231–244 (1996).

Chang et al., "Laser Vaporization/Ionization Interface for Capillary Electrophoresis—Time–of–flight Mass Spectrometry," 69:2251–2257 (1997).

Hardin et al., "Laser Ionization Mass Spectrometry of Nonvolatile Samples," Anal. Chem. 53:1492–1497 (1981).

Hardin et al., "Laser Desorption Mass Spectrometry with Thermospray Sample Deposition for Determination of Nonvolatile Biomolecules," Anal. Chem. 56:2–7 (1984).

Hayes et al., "Moving Belt Interface with Spray Deposition for Liquid Chromatography/Mass Spectrometry," Anal. Chem. 55:1745–1752 (1983).

Jespersen et al., "Attomole Detection of Proteins by Matrix–assisted Laser Desorption/Ionization Mass Spectrometry with the Use of Picolitre Vials," Rapid Communications in Mass Spec. 8:581–584 (1994).

McGuire et al., "On–Line Fast Atom Bombardment Mass Spectrometric Detection in High–Speed Countercurrent Chromatography Through a Moving Belt Interface," Chapter 12, Modern Countercurrent Chromatography, American Chemical Society, (1995).

Murray et al., "Coupling Matrix–assisted Laser Desorption/Ionization to Liquid Separations," 16:283–299 (1997).

Nagra et al., "Liquid Chromatography–time–of–flight Mass Spectrometry with Continuos–flow Matrix–assisted Laser Desorption Ionization," 711:235–245 (1995).

Sheehan et al., "Low Pressure Electrospray" In proceedings of The 15th ASMS Conference on Mass Spectrometry and Allied Topics, Palm Springs, CA, Jun. 1–5, (1997).

Stevenson et al., "A Simple Off–Line Sample Spotter for Coupling HPLC with MALDI MS," 16:54–60 (1998).

Vorm et al., "Improved Resolution and Very High Sensitivity in MALDI TOF of Matrix Surfaces Made by Fast Evaporation," 66:3281–3287 (1994).

Weinberger et al., "An Evaluation of Crystallization Methods for Matrix–assisted Laser Desorption/Ionization of Proteins," In Proceedings of the 41st ASMS Conference on Mass Spectrometry and Allied Topics, San Francisco, CA, May 31–Jun. 4, (1993).

Zhang et al., "Capillary Electrophoresis Combined with Matrix–Assisted Laser Desorption on a Matrix–Precoated Membrane Target," J. Mass. Spec. 31:1039–1046 (1996).

Jungclas et al., "Fractional Sampling Interface for Combined Liquid Chromatography–Mass Spectrometry with $^{252}$Cf Fission Fragment–Induced Ionization," J. Chromatography 271:35–41 (1983).

* cited by examiner

ON-LINE AND OFF-LINE DEPOSITION OF LIQUID SAMPLES FOR MATRIX ASSISTED LASER DESORPTION IONIZATION-TIME OF FLIGHT (MALDI-TOF) MASS SPECTROSCOPY

CROSS REFERENCE TO RELATED APPLICATIONS

This application claims priority from provisional Patent Application No. 60/047,489, filed May 23, 1997, and is a continuation-in-part from U.S. patent application Ser. No. 09/083,815, filed May 22, 1998, now U.S. Pat. No. 6,175,112 the whole of which are hereby incorporated by reference herein.

STATEMENT REGARDING FEDERALLY SPONSORED RESEARCH OR DEVELOPMENT

Part of the work leading to this invention was carried out with United States Government support provided under a grant from the National Institute of Health, Grant No. NIH (GM15847). Therefore, the U.S. Government has certain rights in this invention.

BACKGROUND OF THE INVENTION

One of the most important challenges facing analytical chemistry today is analysis of biological samples. A successful technique should handle an immense number of samples in a short time and be compatible with existing liquid-phase chemical and separation techniques.

One of the most useful analytical methods for biological samples is mass spectroscopy. Liquid samples can be introduced into a mass spectrometer by electrospray ionization (1), a process that creates multiple charged ions. However, multiple ions can result in complex spectra and reduced sensitivity. A more preferred technique, matrix-assisted laser desorption time-of-flight mass spectrometry (MALDI-TOF MS) (2), has received prominence in analysis of biological polymers for its excellent characteristics, such as ease of sample preparation, predominance of singly charged ions in mass spectra, sensitivity and high speed. In principle, a mixture of analytes with excess matrix is deposited onto a probe and irradiated by a short laser pulse. Matrix molecules, which absorb most of the laser energy, transfer that energy to analyte molecules to vaporize and ionize them. Once created, the analyte ions are analyzed in mass spectrometer, typically a TOF mass spectrometer.

MALDI is typically operated as an off-line ionization technique, where the sample, mixed with a suitable matrix, is deposited on the MALDI target to form dry mixed crystals and, subsequently, placed in the source chamber of the mass spectrometer. Although solid samples provide excellent results, the sample preparation and introduction into the vacuum chamber requires a significant amount of time. Even simultaneous introduction of several solid samples into a mass spectrometer or off-line coupling of liquid-phase separation techniques with a mass spectrometer do not use TOF mass spectrometer time efficiently. In addition, MALDI-MS analysis typically requires finding the "sweet spot" on the sample target, so that a reasonable signal can be obtained (5,6). Although a motorized xy stage may be incorporated for automated searching for the spot providing the best spectrum, this procedure can be a time consuming step.

To improve on these procedures, microfabricated targets have recently been developed for automated high throughput MALDI analysis (7,8). In these designs, pL-nL sample volumes can be deposited into a microfabricated well with dimensions similar to the spot size of the desorbing laser beam (~100 $\mu$m diameter). Thus, the whole sample spot can be irradiated and the search for the "sweet spot" eliminated. Analysis of short oligonucleotides has been demonstrated with ~3.3 s required to obtain a good signal to noise ratio for each sample spot (8). Although the total analysis time, including the data storage, required 43 min, theoretically all 96 samples could be recorded in 330s.

While the miniaturization of the sample target simplifies the static MALDI analysis, on-line coupling would allow continuous analysis of liquid samples including direct sample infusion and the monitoring of chromatographic and electrophoretic separations. Compared to ESI, MALDI provides less complex spectra and, potentially, higher sensitivity. There have been numerous reports in the literature about the MALDI analysis of flowing liquid samples. In one arrangement, the sample components exiting a CE separation capillary were continuously deposited on a membrane presoaked with the matrix and analyzed after drying (9,10, 11,12). In other cases, the liquid samples were analyzed directly inside the mass spectrometer using a variety of matrices and interfaces. For example, a nebulizer interface was used for continuous sample and matrix introduction (13-19). MALDI was then performed directly off rapidly dried droplets. In another design, a continuous probe, similar to a fast atom bombardment (FAB) (20) interface, was used for the analysis of a flowing sample stream with liquid matrix (21-24). Glycerol was used to prevent freezing of the sample. Other attempts for liquid sample desorption were also made using fine dispersions of graphite particles (25, 26,27) and liquid matrices (2,28-40) instead of a more conventional matrices. More recently, an outlet of the capillary electrophoresis column was placed directly in the vacuum region of the TOF mass spectrometer (41). The sample ions, eluting in a solution of $CuCl_2$, were desorbed by a laser irradiating the capillary end. On-line spectra of short peptides separated by CE were recorded. Attempts to use ESI to introduce liquid sample directly to the evacuated source of a mass spectrometer have also been reported (42-44).

Although the above-listed examples show efforts to address various different problems related to the analysis of flowing liquid samples, currently there is no universal MALDI interface that would address the need for simple and sensitive analysis of minute sample amounts and, furthermore, that would permit simultaneous, on-line processing of multiple samples. A generally useful procedure and a universal interface for continuous introduction of an individual or multiplexed liquid sample or samples into a time-of-flight mass spectrometer so that on-line MALDI-MS analysis can be carried out would be highly desirable. In addition, a general method for sample preparation that would permit homogenous deposition of small quantities of a sample with improved reproducibility would also be valuable.

BRIEF SUMMARY OF THE INVENTION

In one aspect, the invention is directed to a universal interface and sample load mechanism for continuous on-line liquid sample introduction directly to a mass spectrometer at subatmospheric pressure. Preferably, the liquid sample includes a matrix, either solid or liquid, for use in matrix-assisted-laser-desorption-ionization, most particularly in a time-of-flight mass spectrometer which can further promote throughput and utility of MALDI-TOF MS. In this method of the invention, the same samples and matrices, both solid and liquid, can be used as in conventional MALDI. In practice of this method, a solution of sample containing, e.g., peptide and matrix is infused directly into the source chamber of a mass spectrometer at subatmospheric pressure, deposited on a moving sample holder, such as a rotating quartz wheel, and desorbed by, e.g., a nitrogen laser. The system and method of this aspect of the invention are particularly amenable to multiplexing because of the possibility of parallel deposition of multiple samples, e.g., from a capillary array or microchip channels, with subsequent sequential desorption with a scanned laser beam. This format is particularly useful for high throughput MS analysis.

Extremely rapid evaporation of solvent results in formation of a thin and narrow sample trace. This sample uniformity results in excellent spot-to-spot reproducibility and detection limits in the attomole range, or lower. The interface is suitable for rapid analysis of small sample amounts and allows on-line coupling of microcolumn separation techniques with mass spectrometers.

In another aspect, the invention is directed to an off-line method of preparing a sample for analysis at subatmospheric pressure in a deposition chamber, for use with any analysis system. The method results in the homogeneous deposition of small quantities of sample with improved reproducibility. In practice of this method of the invention, a sample solution, with or without matrix, is introduced through an infusion device into a deposition chamber maintained at subatmospheric pressure and deposited directly onto a sample receptor in the chamber. The sample receptor with the deposited sample can then be placed into the source chamber of a mass spectrometer, or the sample can be used, e.g., as a substrate for any suitable reaction such as staining or immunochemistry.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

DESCRIPTION OF THE PREFERRED EMBODIMENTS OF THE INVENTION

A. On-Line Sample Analysis

A moving surface interface for universal MALDI analysis of flowing samples has now been developed. In use, the interface of the invention permits deposition of a liquid sample stream onto a moving surface inside the vacuum region of a mass spectrometer, and in particular, a time-of-flight mass spectrometer (TOF-MS instrument). The design of the interface permits easy handling of very small (submicroliter) sample volumes and minimizes sample losses both during handling and desorption. The interface and on-line processing method of the invention take advantage of the significant experience available in the field of MALDI.

Figure 1A:
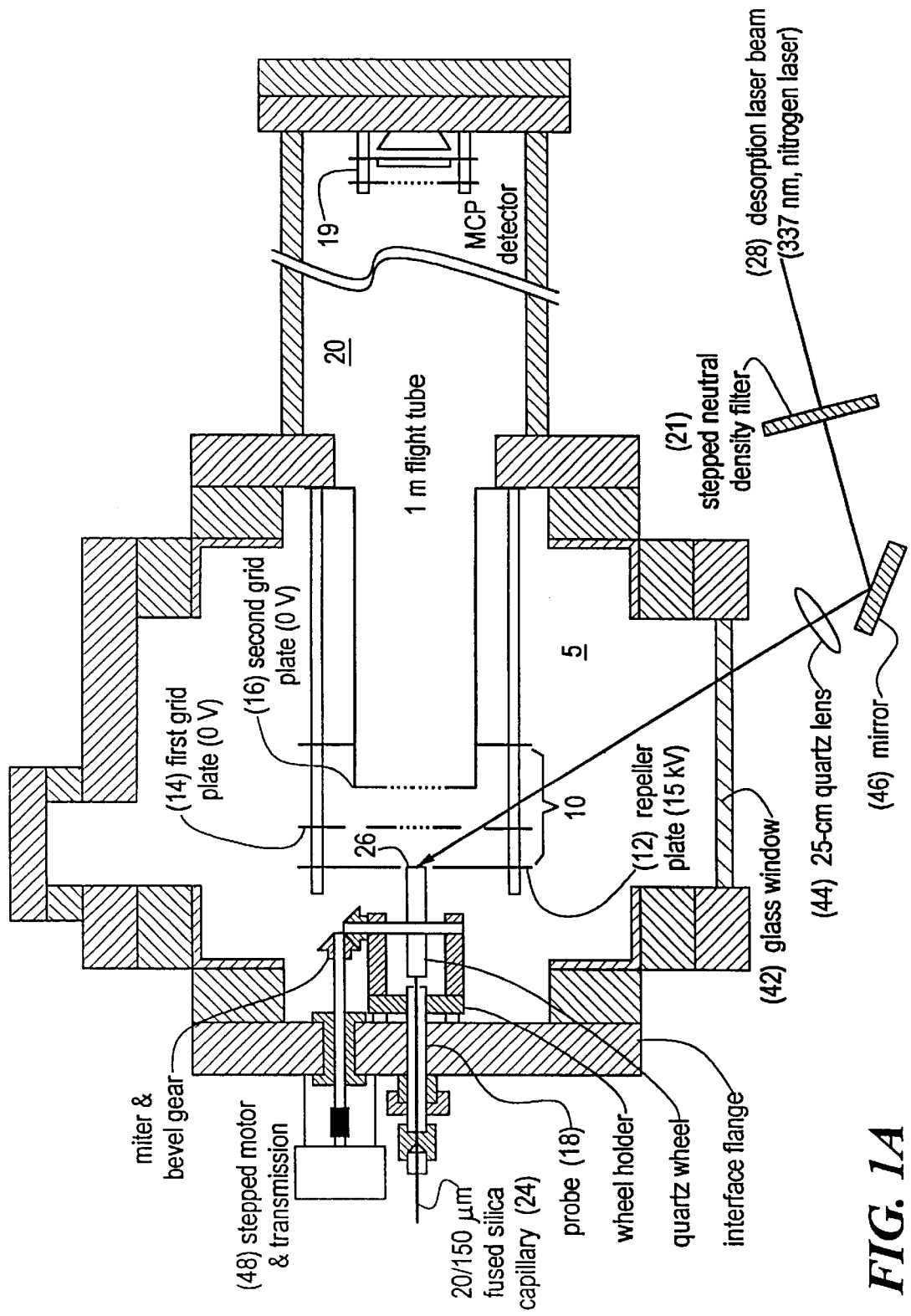
FIG. 1A is a plan view of an on-line MALDI-TOF MS instrument incorporating a sample load mechanism for practicing a method of the invention.

As shown in FIG. 1A, the two essential elements of a TOF mass spectrometer are the source chamber 5, within which is an acceleration (extraction) region 10, and the flight region 20. The electric field in the acceleration region is given by the voltage difference between the repeller 12 and the acceleration plate 14. A second acceleration plate 16 and additional ion optics may also be used. In a conventional instrument, ions formed at the probe tip 18 by MALDI are extracted towards the acceleration plate. Because of differences in their masses, different ions are accelerated to different velocities during their stay in the acceleration region. Thus, light ions move across the field-free (flight) region in a shorter time than do heavy ones. An ion signal from the detector is recorded as a function of time and can be transformed to a function of ion mass-to-charge ratio (mass spectrum). The entire spectrum typically may be recorded in less than 100 $\mu$s. Analysis of small molecules is even faster. Alternatively, ions may be created by simple laser desorption/ionization; i.e., no matrix has to be added.

Figure 1B:
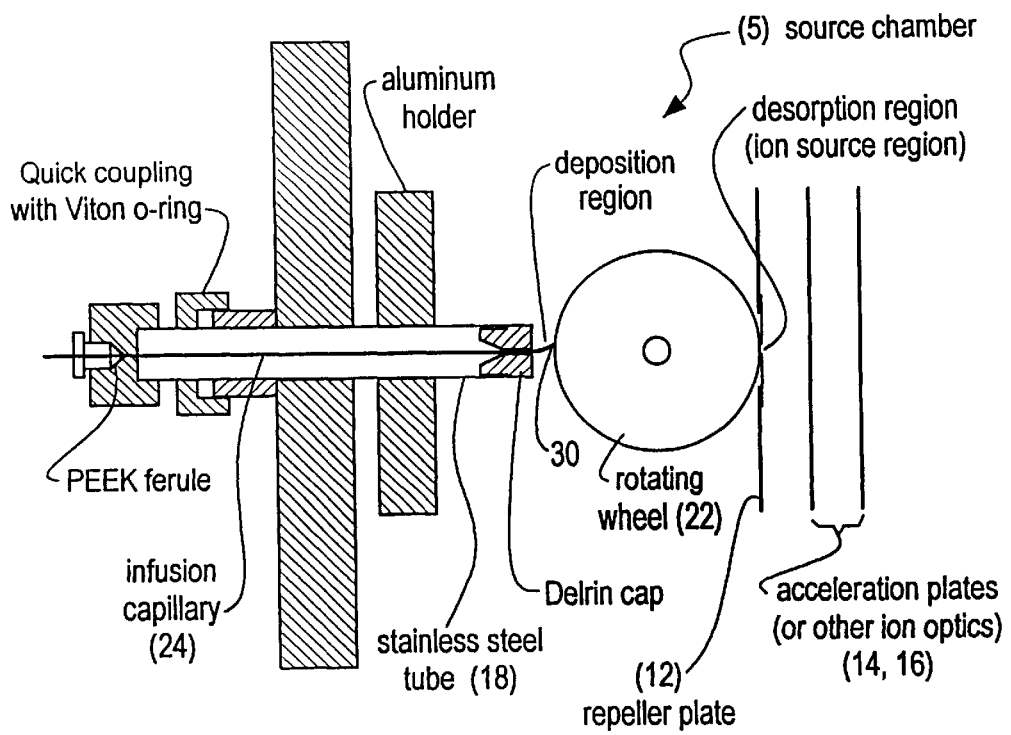
FIG. 1B is a schematic partial side view of the sample load mechanism of the mass spectrometer of FIG. 1A.

Referring now to FIGS. 1A and 1B, as will be explained in more detail below, in the on-line processing method of the invention, a liquid sample emerging from the probe tip 18 is deposited under vacuum onto a moving sample receptor, e.g., a rotating quartz wheel, directly in the source chamber of the mass spectrometer. The analyte, premixed with the suitable matrix, is deposited directly onto the quartz wheel 22 through a narrow fused silica capillary 24. Typically, a 20 $\mu$m i.d. (150 $\mu$m o.d.)×10 cm capillary is used resulting in sample flow rate of ~300 nl/min. At this flow rate, the sample immediately dries on the wheel, forming a continuous trace ~40–60 $\mu$m wide and only few hundred nanometers thick. The wheel rotation then brings the sample trace towards a slit 26 in the repeller plate 12, where it is irradiated and desorbed by the desorption nitrogen laser 28.

Sample Deposition Process.

In order to understand the deposition process of the invention (under vacuum), experiments were performed in a small cylindrical vacuum cell or deposition chamber. The deposition process could be observed visually, and any changes in conditions could easily be implemented. Deposition was carried out at a pressure of 1 Torr, which condition was assumed to be similar to deposition under high vacuum. A pressure of 1 Torr is significantly lower than the vapor pressure of common solvents at room temperature. Therefore, the solvent in liquid phase is far from equilibrium with the gaseous phase at $10^{-6}$ Torr as well as at 1 Torr, resulting in extremely fast evaporation of the solvent at either pressure range.

Figure 2A:
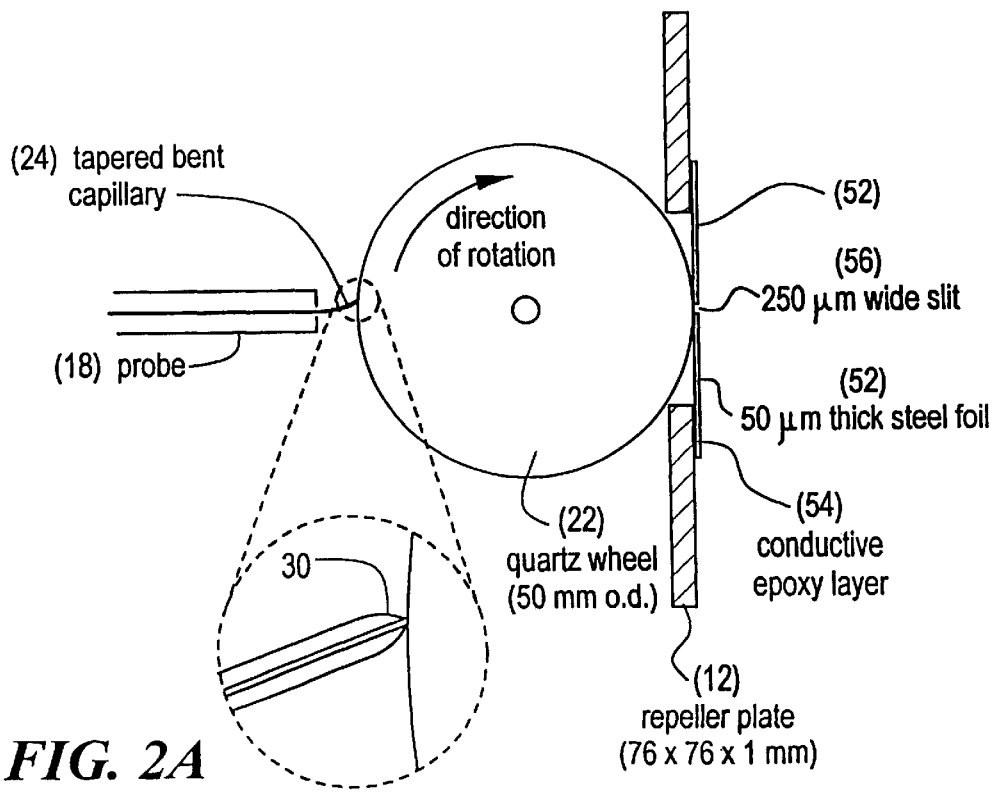
FIG. 2A is a detail schematic view of FIG. 1B showing the liquid deposition process on the rotating wheel within the vacuum of the mass spectrometer of FIG. 1A.
Figure 2B:
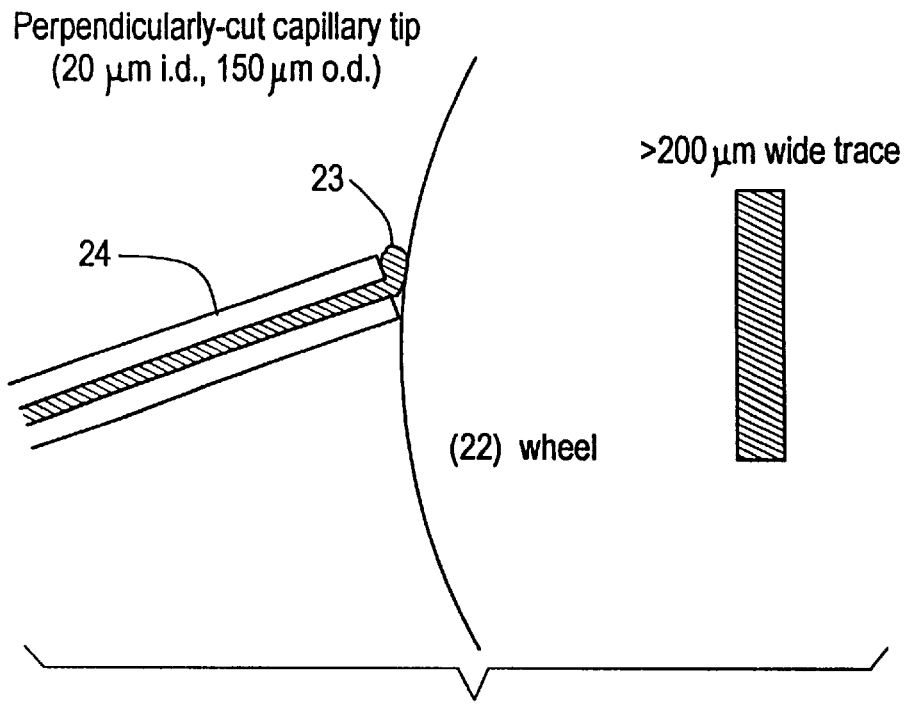
FIGS. 2B and 2C are close up views of the liquid deposition process of FIG. 2A from a perpendicularly-cut capillary and a tipped capillary, respectively, along with the corresponding sample traces formed.

Solutions of 10 mM methyl green in methanol, water or 50% (v/v) methanol were deposited on a plastic wheel (either TEFLON® or the acetyl resin DELRIN®, DuPont) rotating at ~1 rpm. As can be seen in FIGS. 1B, 2A and 2B, the capillary 24 was bent at the wheel 22 to ensure good contact between the tip 30 and the wheel surface inside the source chamber 5. As can be seen in more detail in FIG. 2A, the tip 30 of capillary 24 was tapered to prevent accumulation of deposited solution on the outer capillary wall and clogging of the capillary. The deposited dye trace on a TEFLON wheel formed a series of stains rather than a uniform trace. On the other hand, a uniform trace of the dye was found when a DELRIN wheel was used. This result was likely due to the lower hydrophobicity of DELRIN relative to TEFLON, and perhaps due to the fact that the surface of DELRIN was not as polished. No spraying of the dye inside the chamber was observed, indicating that virtually all of the sample adhered to the wheel.

In order to determine the liquid flow rate in the capillary, water was infused on the DELRIN wheel rotating at ~1 rpm. A 6-cm portion of the outer protective polyimide coating of the infusion capillary (20 $\mu$m i.d., 150 $\mu$m o.d., 12 cm length) was removed on the column outside the vacuum chamber. A short plug of 10 mM aqueous methyl green solution was injected into the water stream, and the time that the color zone needed to pass over a 5.0 cm distance in the capillary was measured. The velocity of water in the infusion capillary was determined to be 10.6±0.7 mm/s, and the corresponding flow rate was 200±20 nL/min. The flow was also calculated from the Poiseuille equation, $F=\pi \Delta p r^4/(8\eta \, l)$, where the pressure difference, $\Delta p=101$ kPa; capillary radius, r10 $\mu$m, viscosity at 25° C., $\eta=0.89$ mpa.s and capillary length, l=0.12 m. The theoretical value of the flow rate, 220 nL/min, was in excellent agreement with the measured value. The result also indicated that water evaporation cooled only the very end of the infusion capillary and that water in the capillary was at room temperature.

Sample Morphology.

The preparation of MALDI sample (mixture of analyte and matrix) is known to play an essential role in achieving optimal performance of MALDI-MS analysis. A number of different sample preparation techniques exist, which have been focused primarily on the improvement of sample homogeneity and hence reproducibility of MALDI analysis. In addition to the common dried droplet method (50,51), procedures include slow growing of large crystals (6,52), preparation of microcrystalline matrix substrate by crushing matrix crystals (53) or by fast evaporation (54,55), crystallization under a stream of nitrogen (56,57), or under vacuum (58), and other methods (59–61). Deposition of nano- or picoliter volumes of samples (7,8,62) was also accompanied by fast evaporation of solvent generating smaller crystals of matrix. This latter result led to our selection of the deposition procedure for use in the method of the invention as it would permit the desorption laser to irradiate more crystals, leading to greater uniformity of signal. In addition, during fast evaporation, there is not enough time for solutes to concentrate in the remnants of evaporating solvent, as typically occurs during the dried droplet method (50,51), which results in discrimination effects dependent on spot position (63,64).

Figure 3A:
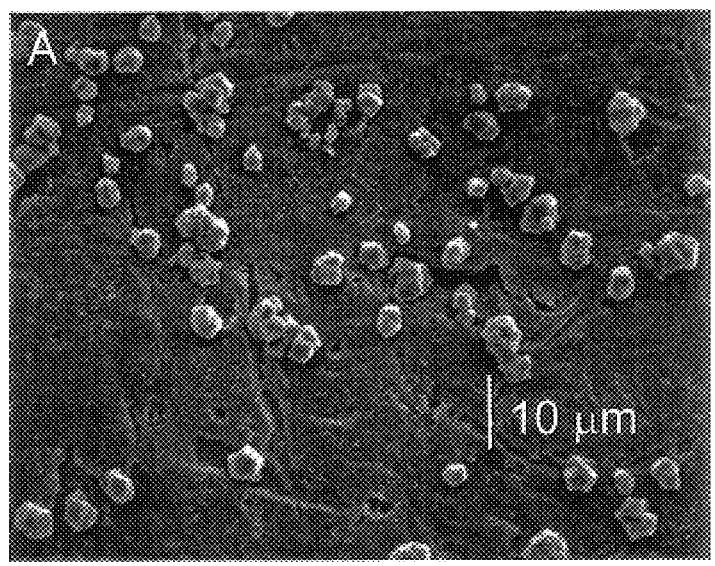
FIGS. 3A–3C are scanning electron micrographs of deposited MALDI sample, luM angiotensin III and 10 mM ACHCA in 50% (v/v) methanol. Preparation of MALDI sample: (3A) dried droplet method, (3B) and (3C) trace of sample deposited at low pressure. SEM characteristics: acceleration voltage 10 kV, sample tilt: 0° (A) and 60° (B,C)

To confirm our choice of sample preparation technique, SEM analysis was first used to examine the morphology of MALDI sample prepared by the dried droplet method. One uL of a mixed solution of 1 $\mu$M angiotensin III and 10 mM $\alpha$CHCA in 50% (v/v) methanol was deposited on an aluminum sample holder and dried at room temperature under atmospheric pressure. As can be seen in FIG. 3A, this conventional preparation of MALDI sample yielded 3–4 $\mu$m crystals scattered over area of 1.5 $\mu$m$^2$. Similar size and shape of the $\alpha$CHCA crystals were reported in the literature (63).

Figure 3B:
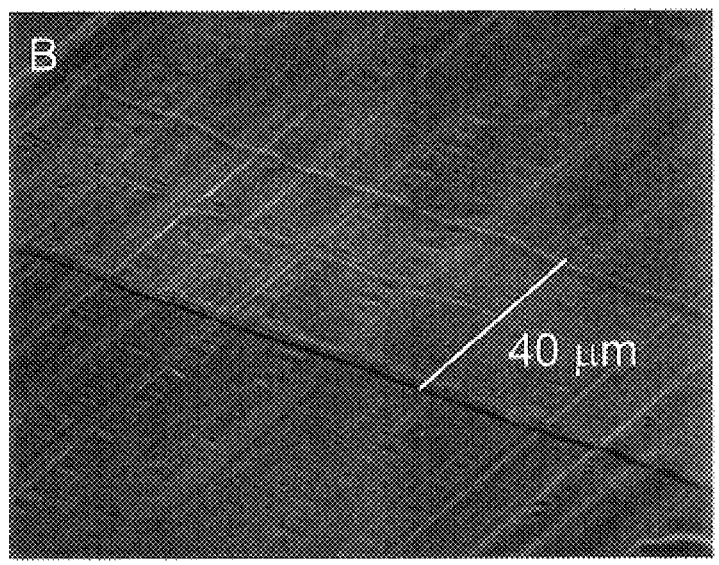
Figure 3C:
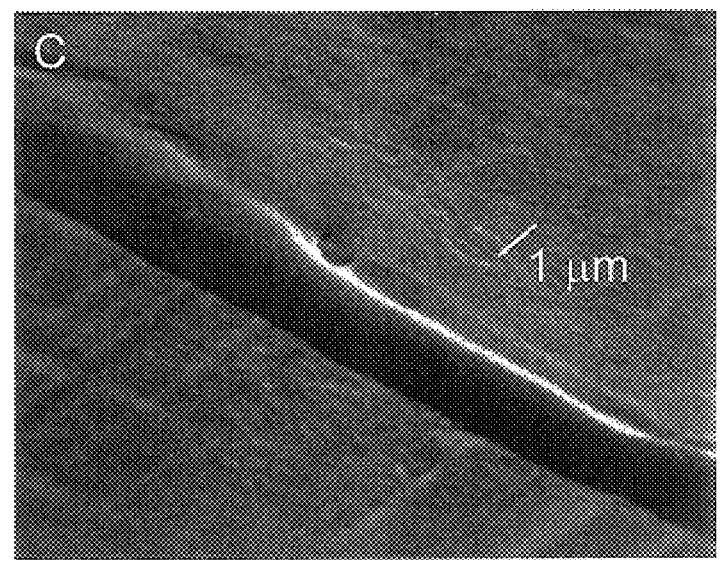

Next, MALDI samples were prepared under vacuum according to the method of the invention. The same mixed solution as above of angiotensin III and ACHCA was deposited on short pieces of self-adhesive copper tape placed on a DELRIN wheel, which was rotating at a speed of 1.0 rpm in the evacuated cell. After deposition and release of the vacuum, the tape was removed from the wheel and placed on a sample holder for SEM. Referring to FIG. 3B, a smooth, 40 $\mu$m wide trace of MALDI sample was observed on the copper surface. It is important to note that with these dimensions, the desorption laser can irradiate all the deposited sample, because the desorption laser spot can be wider than the width of the trace. The subtle grooves perpendicular to the deposited trace, characteristic for the copper tape, can be seen below the deposited sample, indicating a very thin sample film. It can also be seen that the capillary tip scratched the copper and formed a groove in the middle of the trace. Assuming a rectangular profile of the 40 $\mu$m wide trace, a flow rate of 300 nL/min and a matrix density of 1.2 g/cm$^3$, the thickness of the sample film was estimated as ~70 nm. The sample, however, tended to accumulate at the edges, as can be seen in FIG. 3C, with the width of the mound of 1–2 $\mu$m and several hundreds nm in height.

Although the amount of sample was not distributed entirely evenly across the trace, it was distributed regularly along the trace and its morphology was uniform. The fine structure of the sample film above the mound can be compared against bare copper surface, FIG. 3C. The size of the small features in the film structure was ~40 nm; 100 times smaller than the crystals of a conventional MALDI sample. The solvent evaporated and/or sublimated extremely rapidly in the vacuum, leaving an amorphous or microcrystalline sample trace.

The actual sample for on-line MALDI was prepared on an unpolished DELRIN or quartz wheel, whose properties, such as thermal conductivity or surface roughness, were different from those of copper. Nevertheless, the images of the trace deposited on the copper tape could yield useful information on the potential of sample deposition and crystallization in vacuum. The next step was to implement this sample preparation technique into a MALDI-TOF mass spectrometer.

Time-of-Flight Instrument.

Although the preparation of sample for MALDI-MS by deposition in vacuum can be carried out off-line in a separate vacuum chamber, it is most preferably carried out on-line, i.e., in the source chamber of a mass spectrometer. So as to be able to introduce liquid directly into the source chamber of a mass spectrometer and have greater flexibility in the design of the interface, we decided to build a mass spectrometer in house.

High speed pumping was used for the construction of the system in order to maintain pressure sufficiently low during continuous infusion of solvents. A diffusion pump with a pumping speed higher than pumps typical in commercial mass spectrometers was chosen and found appropriate for the task. The large chamber and flight tube ensured fast evacuation speed, as well as sufficient space for modification of the sample loading mechanism. A liquid-nitrogen cryotrap also removed condensable vapors, such as water or methanol from the capillary outlet (pumping speed of 3000 L/s, as specified by manufacturer). The lowest pressure in the flight tube was $5 \times 10^{-8}$ Torr, with a usual pressure in the low $10^{-6}$ Torr range during the deposition of the solvent. It is also possible to remove vapors of the solvent from the spectrometer by differential pumping or use of a refrigerated trap. This would permit reducing the requirements on the pumping speed of the high-vacuum pump (such as a diffusion or turbomolecular pump). In the case of differential pumping, most vapors would be removed by rough pumping at the deposition region (pressures in the mTorr range or, at the most, 1–10 Torr) and the dry sample would be transported to the desorption region, which would be kept at high vacuum, typically $10^{-5}$–$10^{-7}$ Torr. This use of differential pumping is similar in concept to the moving belt interface disclosed in U.S. Pat. No. 4,055,987, in which deposition occurred at atmospheric pressure. However, in the method of the invention, deposition takes place at subatmospheric pressure, which reduces the requirements on the pumping system.

Sample Deposition with MALDI-TOF MS Interface.

On-line deposition of MALDI sample directly in the source chamber of the mass spectrometer was examined and compared with direct infusion into the vacuum. The role of the deposition wheel and its appropriate rotation velocity were observed, and the life expectancy of the infusion capillary (robustness of this sample introduction method) were estimated.

All the following experiments were carried out directly in the source chamber 5 of the TOF MS, as shown in FIG. 1. The process of infusion and deposition of a solution could be conveniently monitored via pressure measurement using an ion gauge. Although the ion gauge was calibrated with air, the sensitivity of the gauge is dependent on the ionization efficiency of gas in the system. Because the relative ionization efficiencies of methanol (1.85) and water (1.12) are higher than that of air (1.00), readout of the ion gauge would include a positive error during infusion of the solvents. Since the composition of the background gas in the chamber varied during the experiment, the ionization efficiency of the gaseous mixture was not precisely known, therefore, the ion gauge signal was plotted in volts, as measured, and not converted to pressure. Nevertheless, an increase of ion gauge voltage is related to an increase of pressure; e.g., an increase of 1V would correspond to a 10-fold increase of pressure at constant composition of background gas. Pressure values given below were estimated from the ion gauge signal if the composition of background gas in the chamber was known.

Figure 4:
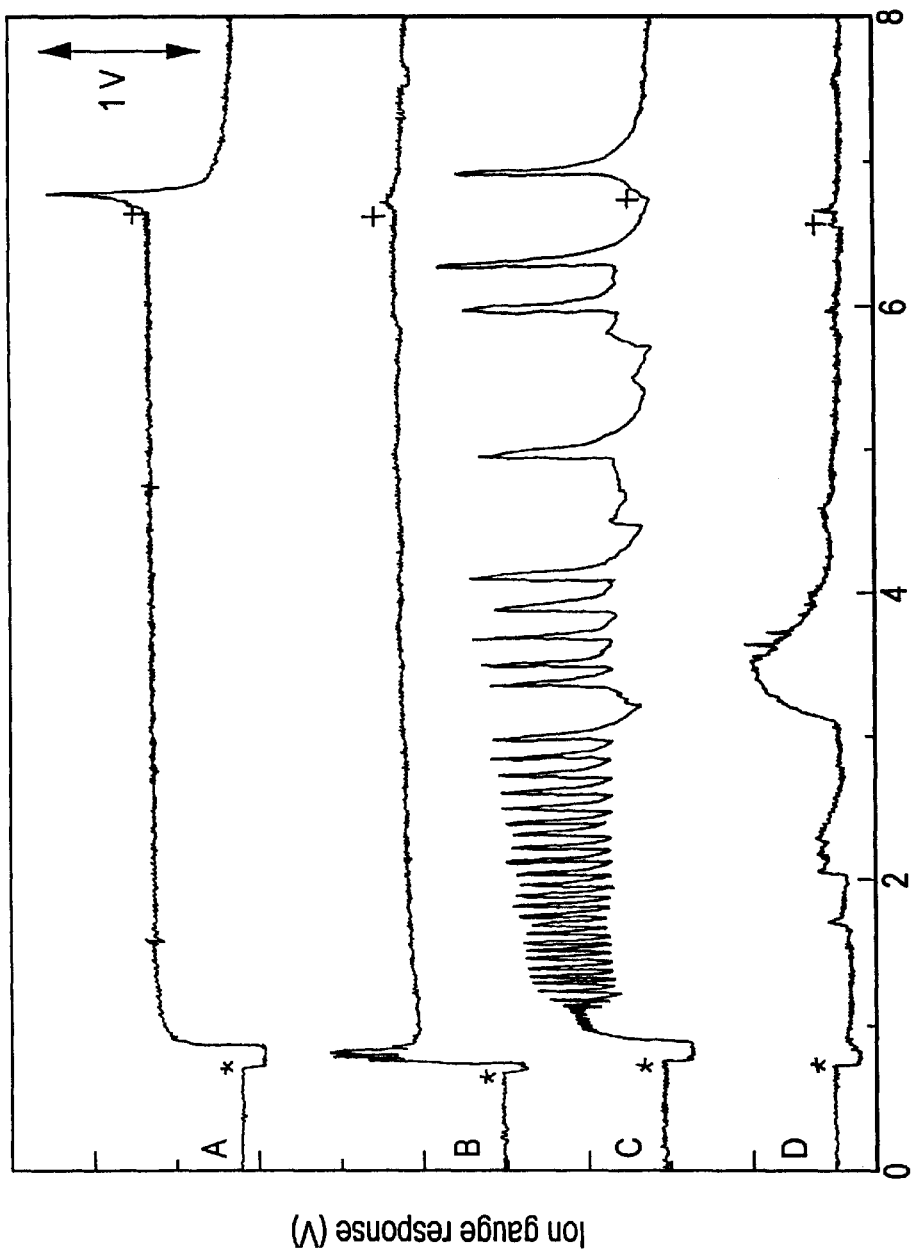
FIG. 4 shows ion gauge signals during deposition of 50% (v/v) methanol (trace A) and infusion of methanol (trace B), 50% (v/v) methanol (trace C) and 10% (v/v) methanol (trace D). Rotation of Delrin wheel 1 rpm (trace A). Beginning of sample infusion marked by *, the end by +.

Infusion and deposition of 50% (v/v) methanol on the quartz wheel (0.5 rpm) resulted in a change of the signal of the ion gauge, as can be seen in trace A of FIG. 4. First, only air flowed through the capillary, and equilibrium between the air infusion and pumping of the diffusion pump yielded a pressure of $\sim 3 \times 10^{-7}$ Torr. A microvial with 50% (v/v) methanol was placed at the capillary inlet at the time marked with the asterisk. The pressure dropped below $2 \times 10^{-7}$ Torr within a second as the air from the capillary was sucked into the chamber during this period. Next, as the solvent filled the capillary, neither air nor solvent eluted from the capillary outlet, and pressure thus remained low. When the solvent reached the capillary outlet, the liquid was deposited on the wheel as a thin film. Evaporation of the solvent from the thin film and the tip of the capillary was extremely fast, as evidenced by a sharp increase in the ion gauge signal. In short order, the rate of infused solvent equaled the rate of methanol that evaporated. Adsorption of the solvent molecules on the walls of the mass spectrometer also reached equilibrium after several seconds, resulting in a pressure plateau ($\sim 2 \times 10^{-6}$ Torr).

The microvial with 50% (v/v) methanol was then removed from the capillary inlet at the time marked with the cross. Air began to flow into capillary, and the flow of solvent increased as the length of the solvent plug in the capillary shortened. This increasing liquid flow resulted in a pressure spike ($<10^{-5}$ Torr). Finally, when all the solvent was removed, air began to flow into the chamber again, and the pressure slowly returned to its original value. This latter process was relatively long, presumably because of slow desorption of the solvent from the walls of the mass spectrometer. Similar pressure behavior was observed for methanol, 10% (v/v) methanol and water (data not shown).

It is interesting to compare the deposition process with straight liquid infusion into the vacuum (traces B–D in FIG. 4), when the capillary tip did not touch the wheel. Infusion of pure methanol caused pressure to increase initially and then to drop somewhat later (FIG. 4, trace B). However, formation of a small droplet was observed at the capillary outlet, diminishing the methanol surface to volume ratio and slowing its evaporation. Evaporation of methanol did not reduce the temperature below its freezing point (-94° C.), so the flow was not interrupted. Partial freezing was assumed when 50% (v/v) methanol was infused, as evidenced by a drop in pressure due to an interruption of the infusion process (FIG. 4, trace C). After the plug melted, the flow was resumed. This cycle repeated several times, causing pressure oscillations. Complete freezing with occasional flow resulted from the infusion of 10% (v/v) methanol or water (FIG. 4, trace D). These results were expected based on the reported studies of others (42,43).

Figure 2C:
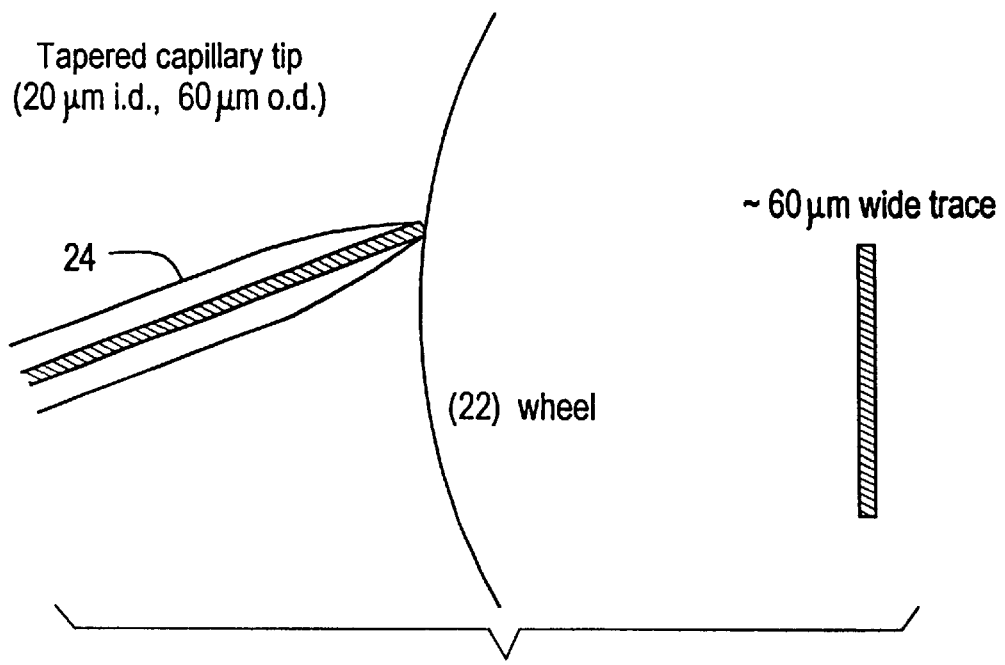

It can be concluded from the results shown in FIG. 4 that the rotating wheel 22 has two important functions. First, as can be seen in FIG. 2C, it prevents accumulation of the solvent at the capillary outlet by transporting the liquid away from the tip. In this regard, it was also found that the capillary end had to be tapered, e.g., by grinding, pulling or etching, because, as indicated in FIG. 2B, evaporation from a solvent droplet 23 hanging on the capillary wall cooled the capillary, causing clogging. Formation of a droplet would also mean increased dead volume and resultant band broadening. In addition, referring again to FIGS. 2B and 2C, it was found that the width of the deposited trace was roughly proportional to the o.d. of the tip. For example, as can be seen in FIG. 2C, the width of a sample trace deposited with a tapered capillary (20 $\mu$m i.d., 150 $\mu$m o.d., 40–60 $\mu$m tip o.d.) was 40–60 $\mu$m, compared to approximately 200 $\mu$m wide sample trace deposited from the same perpendicularly-cut capillary (FIG. 2B). Second, the wheel, which was at room temperature, acted as a heat reservoir preventing the solvent in the capillary outlet from freezing. Energy necessary for evaporation and/or sublimation of the solvent was taken from the wheel as well as from the liquid solvent. Therefore, no additional heating element was necessary in contrast to other designs (21–24, 42). The solvent formed a very thin layer on the surface of the wheel making evaporation and/or sublimation fast and even. This led to thin microcrystalline or amorphous sample films, as shown in FIGS. 3A–3C. Finally, the capillary tube 24 was bent so that the capillary tip 30 pressed the wheel gently, and good contact between liquid exiting the capillary tip and the wheel was maintained.

Additionally, the wheel, made of a nonconductive material, insulated the electrodes inside the mass spectrometer from the outer system. Alternatively, if desired, a conductive metal wheel, made, e.g., of aluminium or stainless steel, may be used so that the capillary tip would be connected electrically to the wheel. This configuration may be useful in studies of arcing. Furthermore, separation of the sample deposition region from the sample desorption region, as a result of mechanical transport of the sample, was advantageous. The solvent, which evaporated at the deposition region, did not contribute to local overpressure at the laser desorption spot. No electrical discharge at the deposition region was thus observed due to elevated local pressure. In addition, separation of the two regions can allow implementation of a differential pumping scheme, in which the deposition region would be maintained under rough vacuum, at subatmospheric pressures of about 1 Torr or less. Another possibility would be to enclose the deposition region by a small refrigerated trap, which would remove the solvent molecules. Frozen solvent could be released from the trap by heating when the instrument was not used.

Washing the infusion capillary with pure methanol between experiments was found to prolong life of the capillary. Methanol likely dissolved ice crystals and other material, such as possible matrix, adsorbed on the tube walls. Filtration of solvents was also found to be useful, as expected. A single capillary (20 $\mu$m i.d., 150 $\mu$m o.d., 12 cm length) could thus be employed for several days of infusion/deposition. In addition, the capillary, left in the spectrometer overnight with inlet exposed to air, did not clog during several months.

Analyte Utilization.

Proper irradiation of sample is essential for obtaining good spectra in MALDI analysis. The entire sample trace area traveling through the desorption region should be irradiated by the desorption laser in order to reach 100%-duty cycle and hence the highest sensitivity. A nitrogen laser is preferred for MALDI analysis. However, use of any type of laser would be possible. A single step of the motor was calculated to expose to the desorption laser a segment portion of sample trace that was 87 $\mu$m long and 40–60 $\mu$m wide. The actual dimensions of the laser desorption spot were measured to be roughly 100×100 $\mu$m. The power density in the laser desorption spot of 500 MW/cm$^2$ would be achieved by 200 $\mu$J, 4 ns pulse of the nitrogen laser, assuming no optical losses. Referring to FIG. 1A, window 42 and lens 44 absorbance, mirror 46 reflectance and non-ideal beam shape of the laser should account for up to 50% attenuation of the laser beam. Since the available desorption power density was still well above 1–10 MW/cm$^2$ necessary for MALDI experiments (2, 65), a neutral density filter was used to adjust the desorption power density to 10–20% above the threshold of the desorption power density.

The range of rotation speed of the wheel 22 given by the stepper motor 48 was 0–12 rpm; however, the usable range of rotation speed was narrower. Clogging of the capillary with frozen solvent and solutes was possible at low speeds, e.g. below ~0.1 rpm. On the other hand, the desorption laser could not irradiate all the sample at high rotation speed, because some segments of the trace would pass the slit in the repeller between laser shots. This means that the number of steps of the motor per second should not be higher than the maximum repetition rate of the laser (30 Hz). Defocusing the laser in order to irradiate a larger area of the sample trace, corresponding to several steps of the motor is not desirable in some cases. For example, if eluent from a separation column is deposited on the wheel, a large laser desorption spot could reduce resolution of the separation method. As will be shown later, several shots (10–50) of the desorption laser should generally be applied to each 87 $\mu$m long segment on the sample trace to analyze more of the deposited sample.

The ratio between the velocity at which analytes enter the capillary and the circumference velocity of the wheel provides a potential means of concentration of the analytes infusing either directly or after separation. When a separation column is coupled to the infusion capillary by means of a liquid junction, the concentration factor of a given analyte is equal to the ratio of the velocity with which the analyte would exit the separation column and the circumference velocity of the wheel. Variation of the rotation velocity of the wheel could change the concentration factor for different compounds during an analysis. For example, broader peaks of slower migrating compounds could be focused by gradual deceleration of the wheel rotation during CE analysis. In practice, in on-line coupling of a separation method, the concentration factor may be decreased because of analyte losses in the liquid junction. Some characteristics of the sample infusion/deposition are shown in Table 1. Even at the lowest rotation speed of the wheel, 0.17 rpm, the number of laser shots per segment of the trace was 6 at maximum repetition rate of the laser. In order to apply more shots to each segment and to use more sample to obtain a better signal-to-noise ratio, a laser with a higher repetition rate would be needed or the rotation speed of the wheel would be lowered after the deposition finished.

TABLE 1

Calculated Deposition Characteristics of Aqueous Solutions.

| Frequency of Motor Steps (Hz) | Rotation Speed (rpm) | Number of Laser Pulses per Segment at 30 Hz Laser Repetition Rate | Concentration Factor for Infusion via 20 $\mu$m i.d. Capillary |
| --- | --- | --- | --- |
| 5 | 0.17 | 6 | 24 |
| 10 | 0.33 | 3 | 12 |
| 15 | 0.50 | 2 | 8 |
| 30 | 1.00 | 1 | 4 |

Flow Rate = 200 nL/min.

It was found to be desirable to clean the wheel after each experiment to remove remnants of the sample. After the source chamber was brought to atmospheric pressure, the probe was pulled out, and a cotton tip applicator soaked with methanol was used to clean the wheel rotating at high speed (>10 rpm). The entire cleaning procedure including subsequent evacuation took less than five minutes. On-line cleaning of the wheel will be necessary in order to use the interface for a long continuous analysis or for multiple analyses.

Materials and Methods

Mass Spectrometer.

Referring to FIG. 1A, a linear Wiley-McLaren type TOF mass spectrometer (46) with a 1 m long drift region was constructed. The 20 cm cubic source chamber 5, sample load mechanism, acceleration optics, 10 cm diameter flight tube 20 and detector 19 were purchased from R. M. Jordan Co., Grass Valley, Calif. Original sample load mechanism was used only to analyze conventional MALDI samples (prepared by dried droplet method). The distances between the repeller plate 12 and the first grid 14 and between the first 14 and the second 16 grids were each 12.7 mm. Ion transmission for each of the two grids, which were grounded, was 90%. The voltage on the repeller plate (+15 kV) was controlled by a power supply (Model CZE1000OR/X2263, Spellman, Hauppauge, N.Y.). A 40 mm dual microchannel plate (MCP) with extended dynamic range (Galileo, Sturbridge, Mass.) served as ion detector. The ion transmission of the detector input grid was 82%, leading to a total ion transmission of the three grids of 66%.

The instrument was evacuated by a diffusion pump (Model VHS-6, Varian, Lexington, Mass.) with a maximum pumping speed of 2,400 L/s. A refrigerated recirculator (Model CFT-75Neslab, Portsmouth, N.H.) was used to cool the diffusion pump. Oil contamination of the mass spectrometer was prevented by a cryotrap (Model 326-6, Varian) and an electropneumatic gate valve (Model GV-8000V-ASA-P, MDC, Hayward, Calif.). The diffusion pump was backed by a two-stage mechanical pump (Model Pascal 2015, Alcatel, Annecy, France) equipped with a molecular seive trap (Model KMST-150-2, MDC). A vacuum controller (Model 307) with two convectron gauges and two ion gauges was purchased from Granvill-Philips, Boulder, Colo. The convectrons were located in the foreline and in the source chamber, and the working ion gauge was in the detector region. A laboratory-built TOF MS controller operated the diffusion pump, electropneumatic gate and HV power supplies. The controller protected the instrument and its components from damage due to an accidental pressure increase or a cooling malfunction. It also contained the voltage supply for the MCP detector.

A 337 nm, 30 Hz nitrogen laser (Model VSL-337ND-S, Laser Science, Franklin, Mass.) was used for MALDI. The laser beam was attenuated with a stepped neutral density filter 21 (Edmund Scientific, Barrington, N.J.) and focused with a quartz lens 44 on the sample target. The angle of incidence of the desorption beam (defined by the beam and the flight axis) was 60°.

On-Line MALDI-TOF MS Interface.

Initial experiments were performed in a small cylindrical vacuum cell made of polycarbonate. The basic arrangement was quite similar to the actual interface described below. Solutions of methyl green were deposited on an acetal resin (DELRIN, DuPont de Nemour, Wilmington, Del.) wheel propelled by a 3V DC motor. The small cell did not contain high voltage electrodes because it was designed only for monitoring of the deposition process. The cell was evacuated by a mechanical pump (Model DD 20, Precision Scientific, Chicago, Ill.).

Referring again to FIGS. 1A and 1B, for the actual on-line MALDI-TOF MS instrument, a mixed solution of analyte and matrix was deposited via a fused silica capillary 24 (Polymicro Technologies, Phoenix, Ark.), 20 $\mu$m i.d., 150 $\mu$m o.d. and 12.0 cm in length, on a quartz wheel 22 (Optikos, Cambridge, Mass.). The capillary was accommodated in a probe 18 made of a stainless steel tube, 9.53 mm o.d., 6.7 mm i.d., 7 cm length. A pipe adapter with a PEEK ferrule, 0.4 mm i.d., was attached to the outer (atmospheric) side of the tube, and a DELRIN cap with a center hole, 0.25 mm i.d., covered the inner (vacuum) side of the tube. The probe was inserted into the source chamber via quick coupling, 9.53 mm i.d., in the center of the interface flange to the point that the end of the capillary was slightly bent while touching the wheel. The outlet of the capillary was tapered, using fine sandpaper. The diameter of the quartz wheel was 5.0 cm and the thickness 1.0 cm; the perimeter surface of the wheel was unpolished. The wheel, which was perfectly balanced on a stainless steel shaft, was propelled by a geared stepper motor 48 (Model ABS, Hurst, Princeton, Ind.), with rotation speeds ranging from 0 to 12 rpm and 1800 steps for 1 full rotation.

The original repeller plate (R. M. Jordan Co.) with a center hole for the sample probe was used only for initial analysis of conventional MALDI samples; modification of the repeller plate was required to incorporate the wheel. Referring to FIG. 2A, a rectangular hole of 12×30 mm was cut in the center of the plate and two pieces 52 of stainless steel foil (25×25×0.05 mm) were glued to the repeller plate 12 with a conductive glue 54 to create a slit (12×0.2 mm) 56 in the center of the plate. The pieces of the foil were glued to the repeller plate at the ends opposite to the slit so that they remained flexible. The distance of the wheel from the interface flange was adjusted such that the wheel was gently touching the stainless steel foil.

Scanning Electron Microscopy (SEM).

Sample morphology was studied on a scanning electron microscope (Model AMR 1000, Amray, Bedford, Mass.). The sample was sputtercoated with gold/palladium (60/40) in a sputtercoater (Model Samsputter 2a, Tousimis, Rockville, Md.). Under the coating protocol, the thickness of the metal coating was estimated to be 10–15 nm.

Experiment Control and Data Acquisition.

A digital delay generator (Model 9650A, EG&G, Princeton, N.J.) triggered the desorption laser as well as a laboratory-built digital divider. The output of the divider drove the stepper motor controller (Model EPC01, Hurst) for precise synchronization of the rotation of the wheel with the laser pulses. By setting the divider ratio, the number of laser pulses applied to each sample spot could be adjusted. The controller of the stepper motor was modified such that external pulses could be received to propel the motor and reset the controller counter. A 500 MHz, 1-Gs/s digital oscilloscope (Model 9350AM, LeCroy, Chestnut Ridge, N.Y.) allowed real time measurement and/or transfer of mass spectra to the computer. A computer program, running under DOS, transferred multiple files from the oscilloscope to a PC via a GPIB interface. Approximately 50 single-shot mass spectra (each consisting of 2000 data points) could be transferred to the computer memory in one second.

Capillary Electrophoresis.

Capillary electrophoresis was performed using 75 $\mu$m i.d. and 375 $\mu$m o.d. fused silica capillaries (Polymicro Technologies) coated with polyvinylalcohol (47) to eliminate electroosmotic flow, with 10 mM solution of citric acid (electrophoresis grade, Schwarz/Mann Biotech, Cleveland, Ohio) as running buffer. Electrophoresis was driven at 500 V/cm by a high voltage power supply (Model PS/EH30, Glassman, Whitehouse Station, N.J.). The sample was injected from unbuffered solution either by electromigration at 50 V/cm or by pressure at 250 Pa. For UV-detection, the total length of the capillary was 15 cm and the effective length 10 cm. Absorbance at 220 nm from a CE detector (Model Spectra 100, Spectra Physics) was recorded using Chrom Perfect (Justice Innovations, Mountain View, Calif.).

Figure 5:
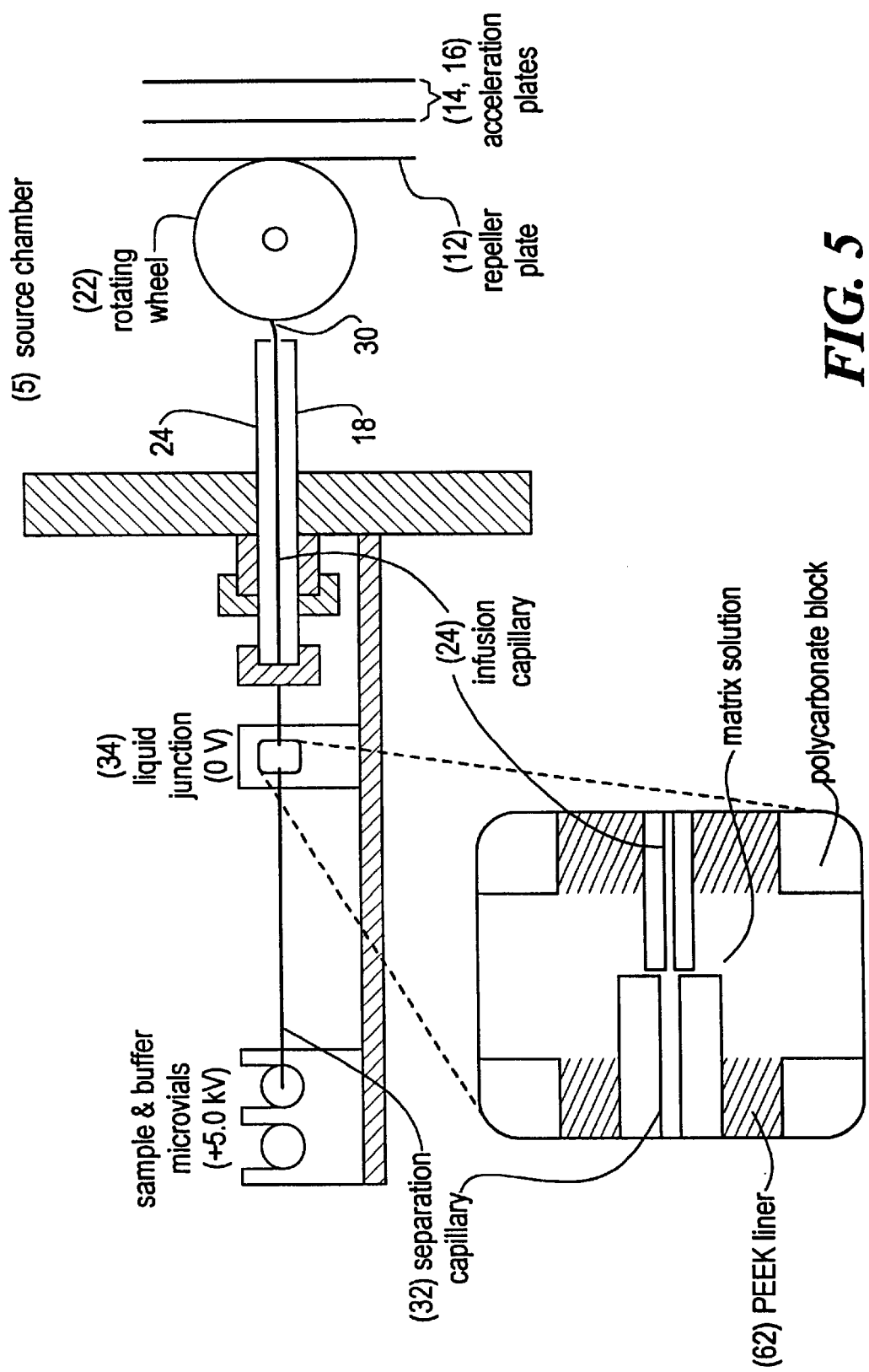
FIG. 5 is a schematic partial side view of an on-line CE-MALDI-TOF MS system for practicing the method of the invention.

Referring to FIG. 5, for on-line MALDI-TOF MS, the separation capillary (10 cm length) 32 was connected to a liquid junction (48, 49) 34 made of polycarbonate, which contained 10 mM of αCHCA matrix as cathodic buffer. PEEK liners 62 (Model FS1L.15 PK and FS1L.4PK, Valco Instruments Co., Houston, Tex.) were inserted into holes in the polycarbonate liquid junction block 34 to center the separation and infusion capillaries precisely, with a gap of approximately 100 pm. The sample was initially injected into the separation capillary, and the stepper motor was activated (0.33 rpm) within 5 seconds.

Chemicals.

Methyl green (Sigma Chemical Co., St. Louis, Mo.) solutions in methanol and distilled water were initially used to explore deposition in a vacuum. α-cyano-4-hydroxycinnamic acid (αCHCA), 2,5-dihydroxybenzoic acid, 4-hydroxy-3-methoxycinnamic (ferulic) acid (all from Sigma Chemical Co.), and 3-hydroxypicolinic acid (Aldrich Chemical, Milwaukee, Wis.) were used as matrices for MALDI, each consisting of 0.1 M stock solutions in 50% (v/v) methanol. Angiotensins, angiotensinogens (see Table 1), heptapeptide EDPFLRF and bovine insulin (BI) were purchased from Sigma Chemical Co and made as 1 mg/mL stock solutions in water. One mM stock solution of BI was prepared by dissolving in 0.1% trifluoroacetic acid (J.T. Baker Inc., Phillipsburg, N.J.). Methanol, ethanol and acetonitrile (all HPLC grade) were purchased from Fisher Scientific, Fair Lawn, N.J.

The following examples are presented to illustrate the advantages of the present invention and to assist one of ordinary skill in making and using the same. These examples are not intended in any way otherwise to limit the scope of the disclosure.

EXAMPLE I

On-line MALDI Performance

Figure 6:
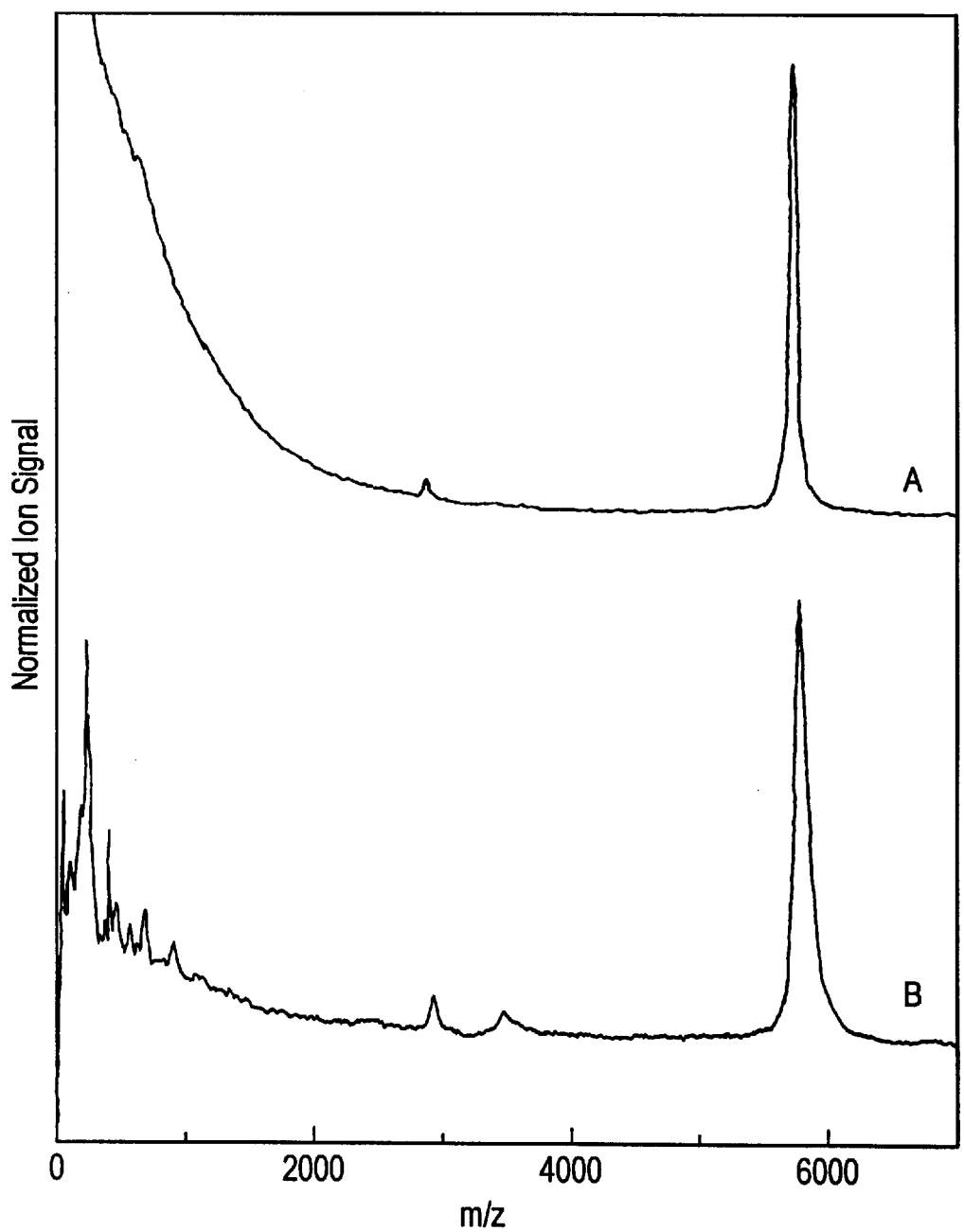
FIG. 6 shows normalized MALDI-MS spectra of bovine insulin with ACHCA matrix. Sample preparation: dried droplet (trace A) and vacuum deposition (trace B)

The performance of the new interface was tested using several oligopeptides with αCHCA as matrix. Off-line MALDI-MS analysis was carried out using the original sample load probe and the repeller. The average of 100 spectra, shown in FIG. 6, trace A, was obtained from a spot on a dried droplet sample of 100 μM bovine insulin and 100 mM αCHCA solution in a mixed solvent (acetonitrile:ethanol:water=36:60:4) deposited on a stainless steel probe tip. For the on-line approach, 1 μM bovine insulin with 10 mM αCHCA aqueous solution was deposited for about 30 seconds on the wheel rotating at 0.33 rpm. In this case, the averaged spectrum was obtained from 100 single shot spectra from 50 segments of the trace, i.e., 2 shots were applied to each segment (FIG. 6, trace B). MALDI spectra of samples of bovine insulin with αCHCA matrix prepared conventionally and by vacuum deposition appeared very similar. Mass resolution of the insulin peak in the case of the vacuum deposited sample was comparable with the value obtained with the original repeller. Improved manufacturing of the repeller plate and incorporation of time-lag focusing should further enhance the resolution. With the use of time-lag focusing, the ions could be accelerated in a more homogeneous electrical field after they travel away from the slit. On-line MALDI spectra of angiotensins and other small peptides with αCHCA matrix were also obtained.

Figure 7:
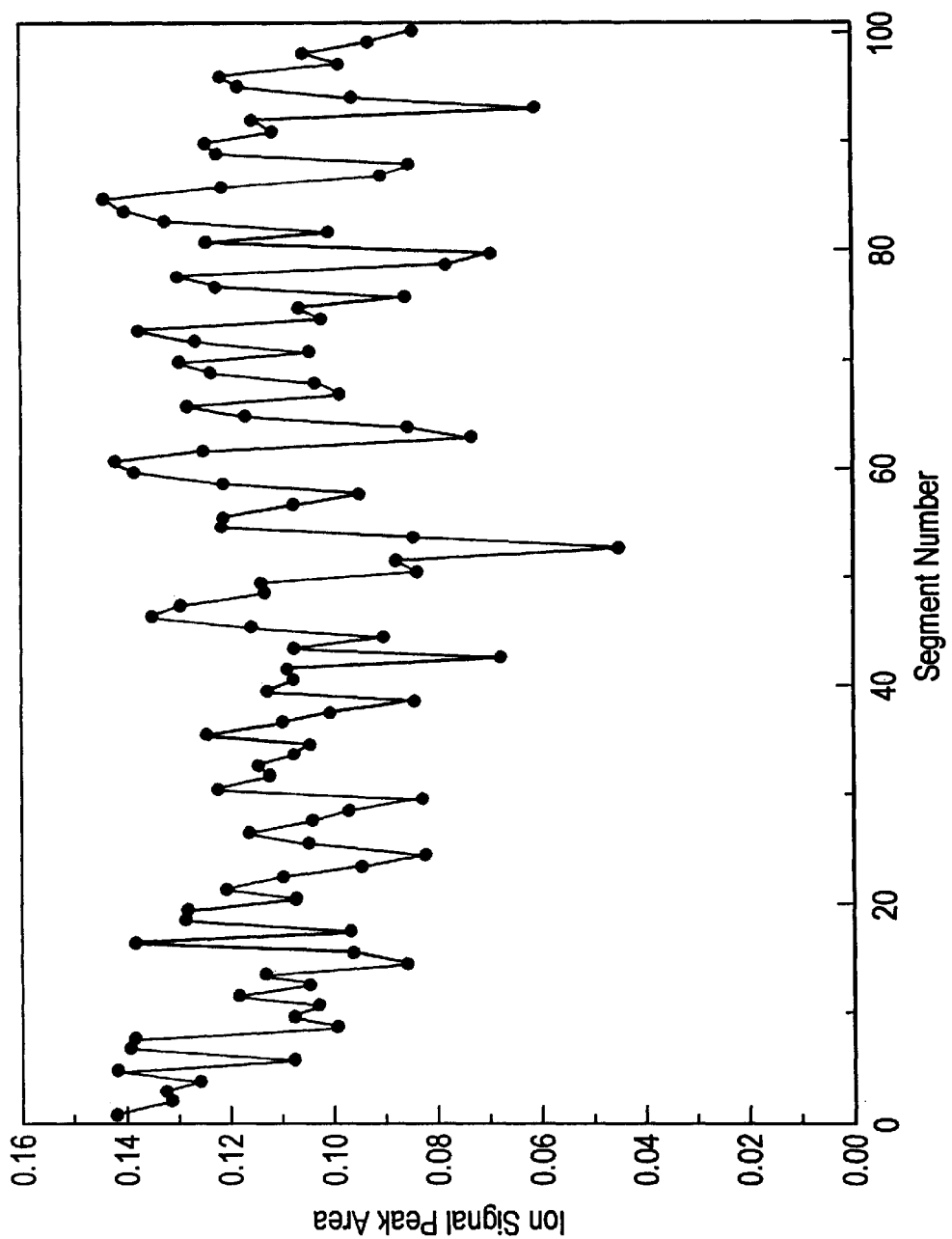
FIG. 7 is a graph showing variations of angiotensin II, frag. 1–7 ion signal versus segment number. Mixed solution of 1 $\mu$M peptide with 10 mM αCHCA deposited on the quartz wheel at 0.33 rpm.

Uniformity of the sample trace over the circumference of the wheel, proper balancing of the wheel and overall ruggedness of the interface are prerequisites for good reproducibility of MALDI spectra, especially with on-line coupling a separation method. In order to determine the variations of MALDI spectra along the trace, a mixed solution of 1 uM angiotensin II, frag. 1–7, and 10 mM αCHCA matrix was deposited on the quartz wheel rotating at 0.33 rpm. The deposition was interrupted after approximately 1 minute, and 1000 single shot spectra were collected at a laser repetition rate of 20 Hz and a rotation speed 0.066, i.e., 10 shots per segment, within 50 seconds. The average of 10 single shot spectra from each of 100 segments was calculated using a PC, and peak areas corresponding to the analyte ion (m/z=900) in the averaged spectra were plotted vs. segment number, as shown in FIG. 7. Although the variations in the signal were ±18%, the ion signal of the peptide was much more constant than the same signal obtained from a conventional MALDI sample. In addition, the peptide peak was present in every single shot spectrum. These results stem from proper alignment of the laser beam with the laser desorption spot so as to encompass the entire segment of the uniform sample trace. In the method of the invention, no search for "sweet spots" is necessary after the initial alignment of the desorption laser beam. In contrast, some spots of a conventional MALDI sample yield no signal at all, and localization of the "sweet spot" on the sample sometimes requires a significant amount of time. Further improvement of signal fluctuations can be achieved using an internal standard.

EXAMPLE II

Effect of Various Matrices

A variety of typical matrices were examined with peptide samples. An important advantage of the on-line interface of the invention is that it can use the same matrices that have been already developed for MALDI and it is not restricted to the liquid matrices. Conventional matrices, such as a-cyano-4-hydroxycinnamic acid, 2,5-dihydroxybenzoic acid, 4-hydroxy-3-methoxycinnamic (ferulic) acid and 3-hydroxypicolinic acid were successfully tested with peptide samples (results not shown).

The effect of the matrix-to-analyte ratio (66) and the presence of alkali metal deserve additional discussion. To study the effects of matrix-to-analyte ratio, a mixed methanolic solution of 1 μM heptapeptide EDPFLRF with 1, 10 or 100 mM ACHCA was deposited on the quartz wheel at 0.33 rpm. It was found that saturated or very concentrated solutions of matrices, such as 100 mM αCHCA solution used in conventional sample preparation, can cause clogging of the capillary. In addition, a very high matrix-to-analyte ratio means thicker sample trace and dilution of the analyte in the matrix. Therefore, use of the matrix solutions at concentrations higher than approximately 10 mM is not recommended for use in our on-line system. The matrix concentration should be reduced even further at very slow rotation speeds of the wheel, when the crystallizing matrix would be removed slowly and thus could accumulate at the capillary outlet.

Figure 8:
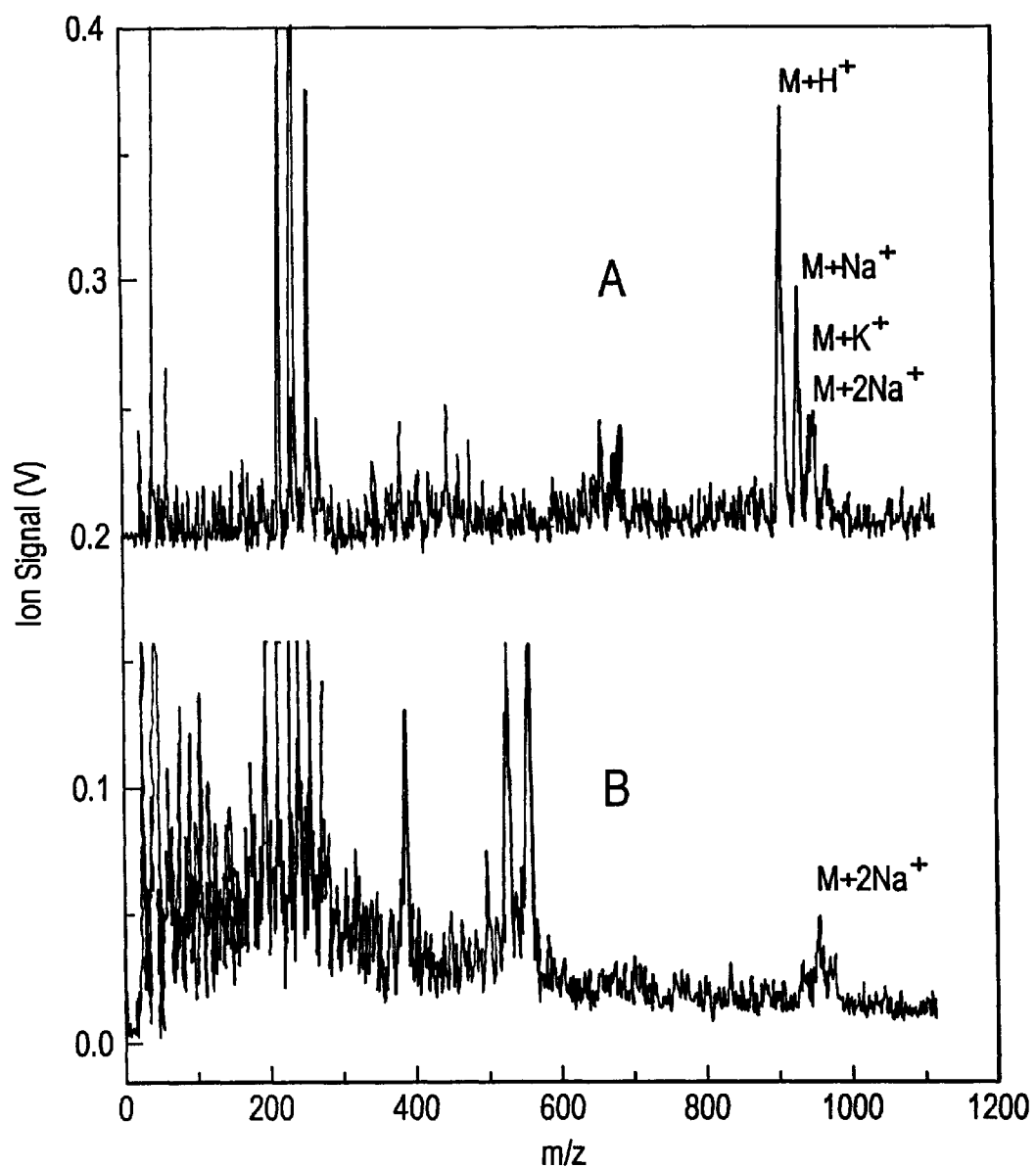
FIG. 8 shows single shot MALDI mass spectra of a mixed solution of 1 pM heptapeptide EDPFLRF with (trace A) 10 mM or (trace B) 1 mM αCHCA matrix deposited on the quartz wheel at 0.33 rpm.

As shown in FIG. 8, trace A, a relatively large peak of analyte can be seen in a single shot MALDI mass spectrum at a matrix concentration of 10 mM. Presumably, it would be advantageous to use matrix at an even lower concentration when a thinner layer of the sample is formed and more analyte should be utilized with a single shot of the desorption laser. However, referring to FIG. 8, trace B only weak peaks associated with the analyte were observed at matrix concentration of 1 mM, although the matrix-to-analyte ratio was sufficient (1,000).

The relative abundance of ions of alkali metal adducts with respect to the pseudomolecular ion of the peptide [M+H]$^+$ suggests an explanation for the low analyte signal at a matrix concentration of 1 mM. Although the peaks of adduct ions, such as $[M+Na]^+$, $[M+K]^+$ and $[M+2Na]^+$, were present in both spectra shown in FIG. 8, they are the prevailing form of analyte ion at lower matrix concentration. This effect is pronounced at low levels of matrix because alkali metals compete with protons from matrix and suppress formation of the protonized form of analyte. There were several possible sources of the alkali metal contamination: peptide, matrix, solvents, the walls of the infusion capillary and wheel. As found later in the CE-MALDI-MS experiment, most of the alkali metals originated from the peptide sample. On-line desalting is essential in order to obtain good quality MALDI mass spectra.

EXAMPLE III

Signal Decay

In order to determine how many shots of the desorption laser will produce optimal mass spectra, a mixed solution of 1 uM angiotensin III with 10 mM αCHCA matrix in methanol was deposited on the quartz wheel rotating at 0.33 rpm. Infusion was interrupted after ~30 seconds, and the wheel was rotated to transfer the sample trace to the desorption region. The desorption power density was adjusted ~20% above the threshold, and 100 shots were applied consecutively to each of 3 neighbor segments on the sample trace. The peak areas corresponding to the analyte ion (m/z=932) were calculated from 100 average spectra (each spectrum was an average of 3 single shot spectra from the 3 segments of the trace) and plotted versus the number of desorption laser shots, as shown in FIG. 8. The first laser shot was found to produce a lower ion signal from the analyte than the next nine laser shots. This result, together with a difference in mass spectra in the low-mass region (not shown), suggests some chemical and physical changes (melting & solidifying) occurring on the sample surface. This behavior of the first shot was variable however, since for some samples, the intensity of the ion signal of the analyte produced by the first shot was similar to that of the consecutive shots. Similar phenomena can also be observed in conventional MALDI (67).

Figure 9:
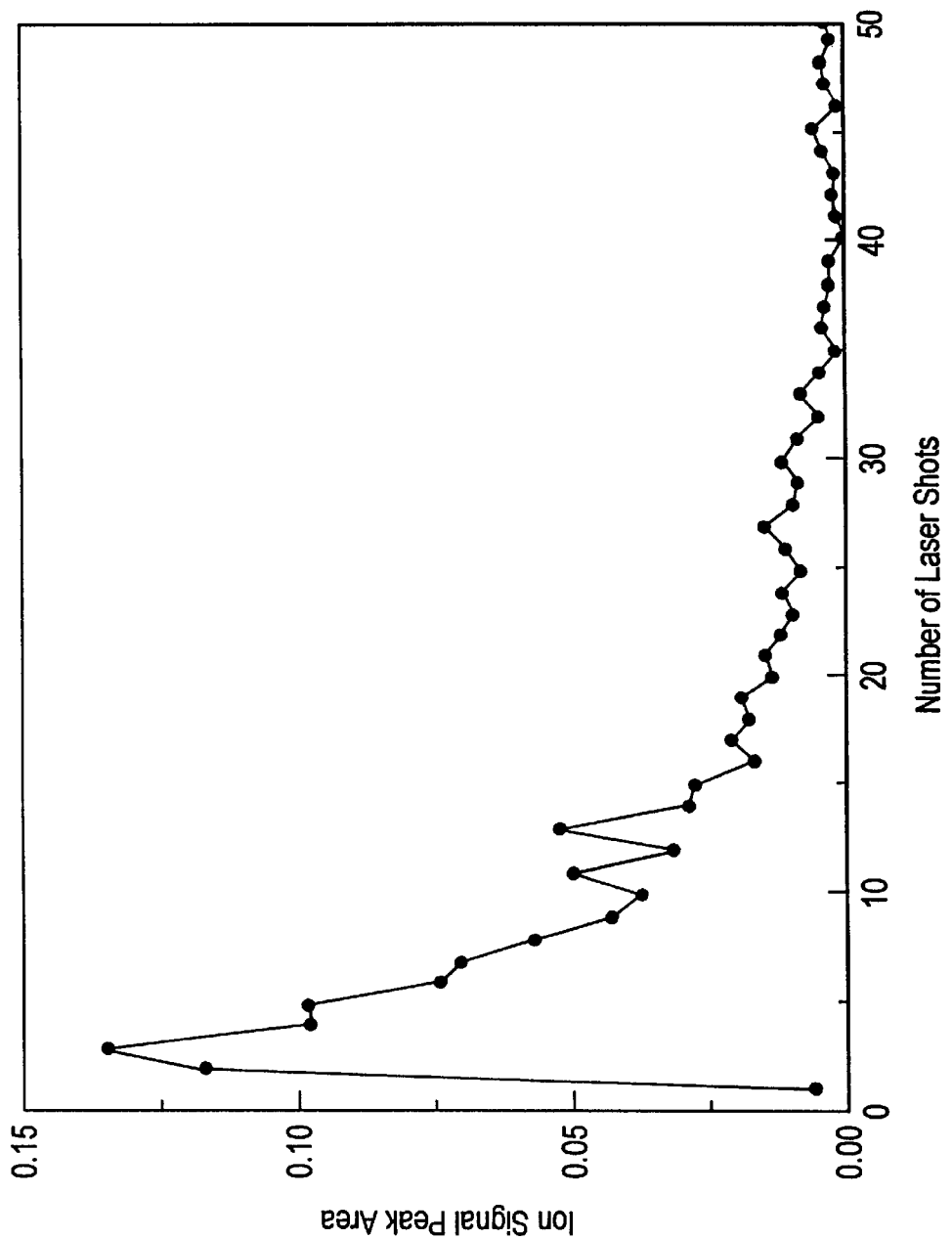
FIG. 9 is a graph showing decay of angiotensin III (m/z=932) signal with number of desorption laser shots applied to the same segment. Mixed solution of 1 $\mu$M angiotensin III with 10 mM αCHCA matrix in methanol deposited on the quartz wheel rotating at 0.33 rpm.

As can be seen in FIG. 9, the ion signal of the analyte produced by the consecutive shots gradually decayed as the sample was removed, with virtually all the sample depleted within 40 laser shots. The results suggest that ~20 single shot spectra should be averaged to obtain the optimum signal-to-noise ratio in this case. Omitting of the first single shot spectrum is generally suggested. It should be pointed out that the number of spectra to be averaged depends on many factors, such as the analyte and matrix concentration and the desorption laser power density. Less spectra may be necessary when the amount of deposited sample is low or the desorption power density is higher.

EXAMPLE IV

Detection of Minute Amounts of Sample

MALDI-MS has already been shown to be a very sensitive method for determination of peptides (7,68). On-line deposition of sample offers additional advantages in sample handling over conventional techniques. Virtually all of the sample solution is transferred to the source chamber and accumulated on the wheel. The segment of the sample trace (given by the width of the trace and a single step of the wheel) is slightly smaller than the spot size of the desorption laser meaning all sample can be used. Several tens of laser shots should utilize all deposited sample because the sample layer is very thin. The interaction of matrix with analyte in solid and gaseous phase during the desorption and ionization should be promoted because the trace consists of well-mixed analyte and matrix. Once the desorption laser beam is properly aligned, the wheel can transport the sample to the desorption region and no "sweet" spot on the sample has to be found.

Figure 10:
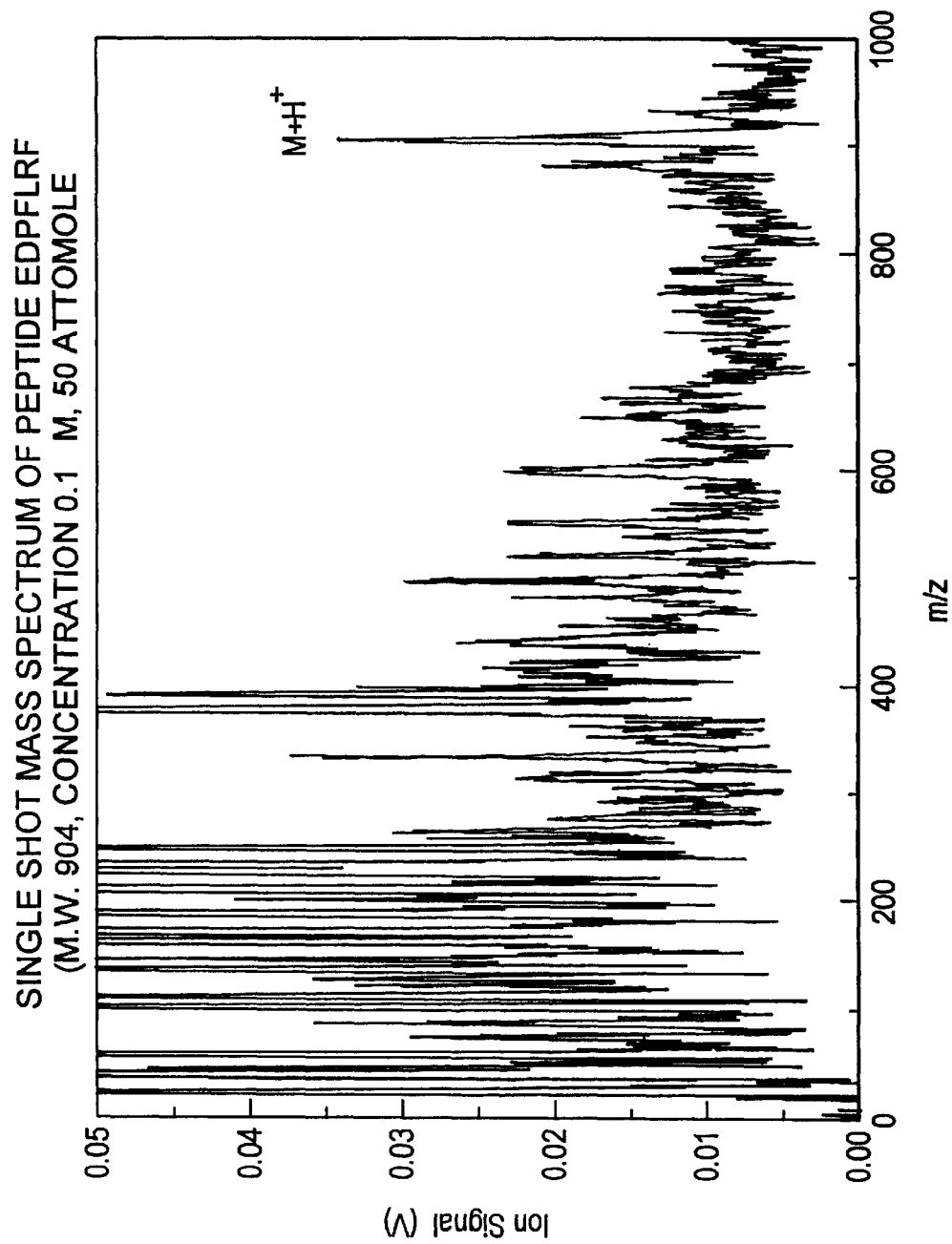
FIG. 10 shows a single shot MALDI mass spectrum of heptapeptide EDPFLRF at a concentration of 0.1 $\mu$M, 50 attomole deposited on the desorption spot.

Referring to FIG. 10, the level of detection possible with a single shot mass spectrum of 50 attomole of the heptapeptide EDPFLRF can be seen is very good.

EXAMPLE V

CE-MALDI-MS

The on-line vacuum deposition of mixed solutions of analytes and matrices offers a powerful approach to conduct separations coupled directly to MALDI-MS. In this experiment, CE-MALDI-MS of a mixture of 300–500 pg of each of 12 angiotensins listed in Table 2, was carried out. A liquid junction was used to connect the separation capillary to the infusion capillary of the interface. Analytes eluting from the separation capillary were mixed with solution of the MALDI matrix in the reservoir of the liquid junction and then drawn into the infusion capillary for deposition on the wheel.

TABLE 2

List of Angiotensins Used for CE-MALDI-TOFMS.

| Peptide | | Structure | Solute number | M.W. | CE-MALDI-MS Migration Time (s) | CE-UV Migration Time (s) |
|---|---|---|---|---|---|---|
| Angiotensin I | Human | DRVYIHPFHL | 1 | 1296.5 | 62.5 | 63.6 |
| | Bullfrog | DRVYVHPFNL | 2 | 1259.4 | 79.1 | 84.0 |
| | Goosefish | NRVYVHPFHL | 3 | 1281.5 | 54.7 | 54.7 |
| | Salmon | NRVYVHPFNL | 4 | 1258.4 | 66.9 | 69.6 |
| | des-Asp$^1$ | RVYIHPFHL | 5 | 1181.4 | 52.5 | 52.5 |
| | [Val$^5$] - | DRVYVHPFHL | 6 | 1282.5 | 62.3 | 63.6 |
| Angiotensin II | Human | DRVYIHPF | 7 | 1046.2 | 73.7 | 78.0 |
| | Frag. 1–7 | DRVYIHP | 8 | 899.0 | 71.7 | 75.6 |
| | Frag. 3–8 | VYIHPF | 9 | 774.9 | 81.1 | 86.4 |
| Angiotensin III | Human | RVYIHPF | 10 | 931.1 | 59.1 | 60.0 |
| Angiotensinogen | Human | DRVYIHPFHLVIHN | 11 | 1760.0 | 60.5 | 60.0 |
| | Porcine | DRVYIHPFHLLVYS | 12 | 1759.0 | 72.7 | 78.0 |

Figure 11:
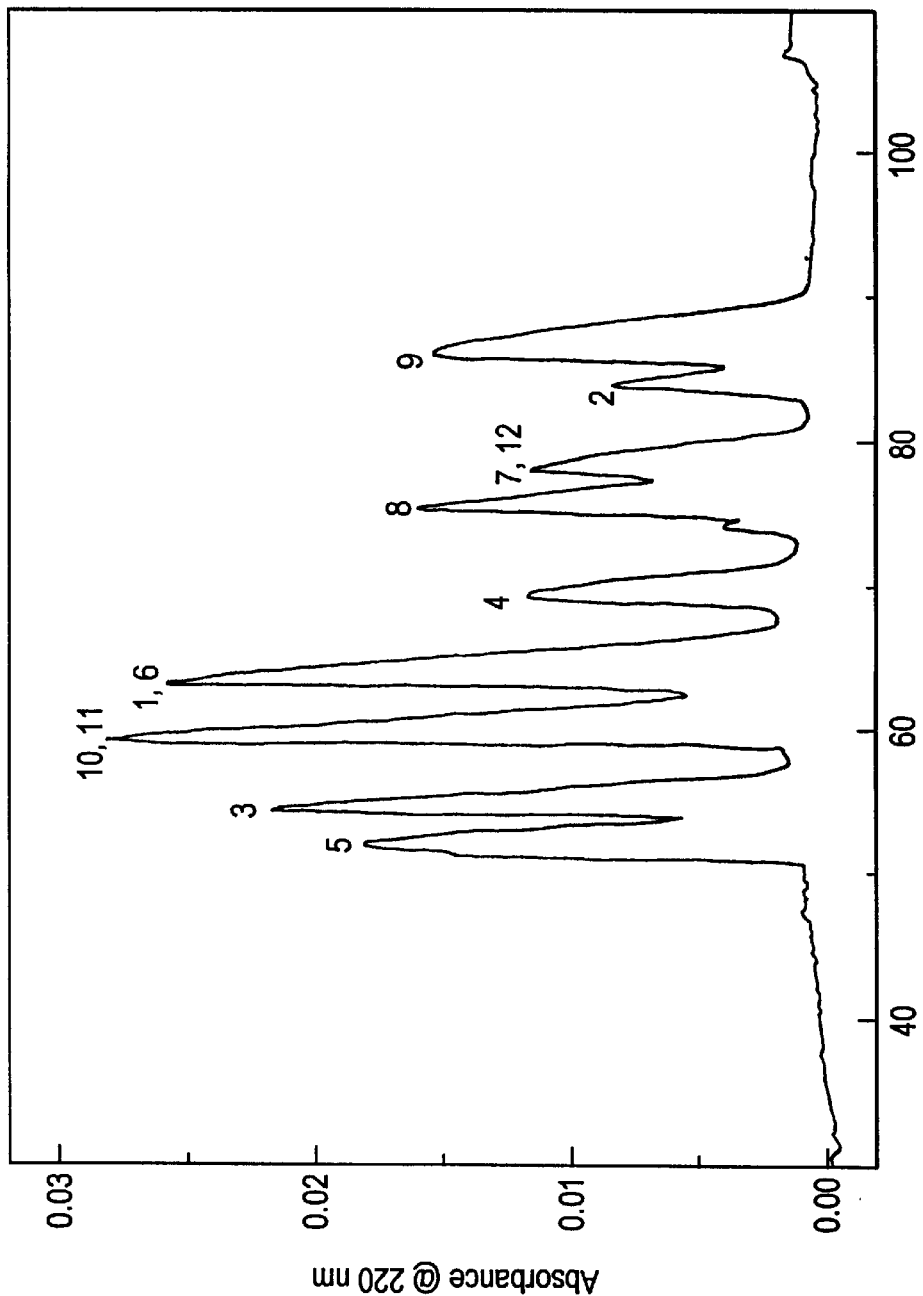
FIG. 11 is a CE-UV electropherogram of angiotensin mixture (see Table 2)

Initially, conventional CE-UV (absorbance detection at 220 nm) was examined. A 10 mM citric acid solution was selected as a running buffer for the separation of the angiotensins because the $pK_a$ and ion mobility of citric acid are similar to that of αCHCA, as estimated from the literature (69) (A 10 mM αCHCA solution in 50% (v/v) methanol will be used in the reservoir of the liquid junction for CE-MALDI-MS.) Angiotensins were injected by electromigration at 50V/cm within 5 s from a 8.3 μg/mL (each) aqueous peptide mixed solution. The final amounts injected ranged from 300 to 500 pg. As shown in FIG. 11, only nine peaks were observed on the electropherogram. The distorted peak shape was caused by the injection of a relatively large amount of sample from an unbuffered solution in order to achieve a high response, given the drifting baseline, probably caused by impurities in the citric acid buffer.

In another CE-UV experiment, a 10 mM αCHCA solution in 50% methanol was placed in the detection reservoir to match the condition of CE-MALDI-MS with the liquid junction. In this case, UV absorption started to increase gradually in the middle of the run due to the migration of UV absorbing anions of αCHCA into the capillary without affecting separation significantly.

In another experiment, αCHCA was used not only as the MALDI matrix but also as the electrolyte in the CE buffer. In this case, indirect detection at 335 nm was used for CE-UV of the angiotensin mixture because of the large ratio between absorption coefficients of matrix and peptides at this wavelength. A 10 mM αCHCA aqueous solution, employed as the CE buffer, strongly absorbed, which resulted in large baseline drifts. Nevertheless, a separation pattern similar to that in FIG. 10 was revealed by indirect detection. Furthermore, there were three additional peaks in the electropherogram due to faster metal cations. This result confirmed that CE separation of the peptides also included desalting of the sample. Although it was found that αCHCA could serve as the electrolyte for CE, citric acid was used instead in CE to show that the conditions of CE separation are not restricted by requirements of MS detection.

For on-line CE-MALDI-MS detection, the infusion flow rate must be high enough to collect all analyte ions migrating out of the capillary (49). In other words, the velocity of the infused solution has to be higher than the electromigration velocity of analyte migrating towards the cathode located in the liquid junction. The infusion flow of 50% (v/v) methanol was about 300 nL/min and most peptide ions were estimated to enter the infusion capillary.

Figure 12:
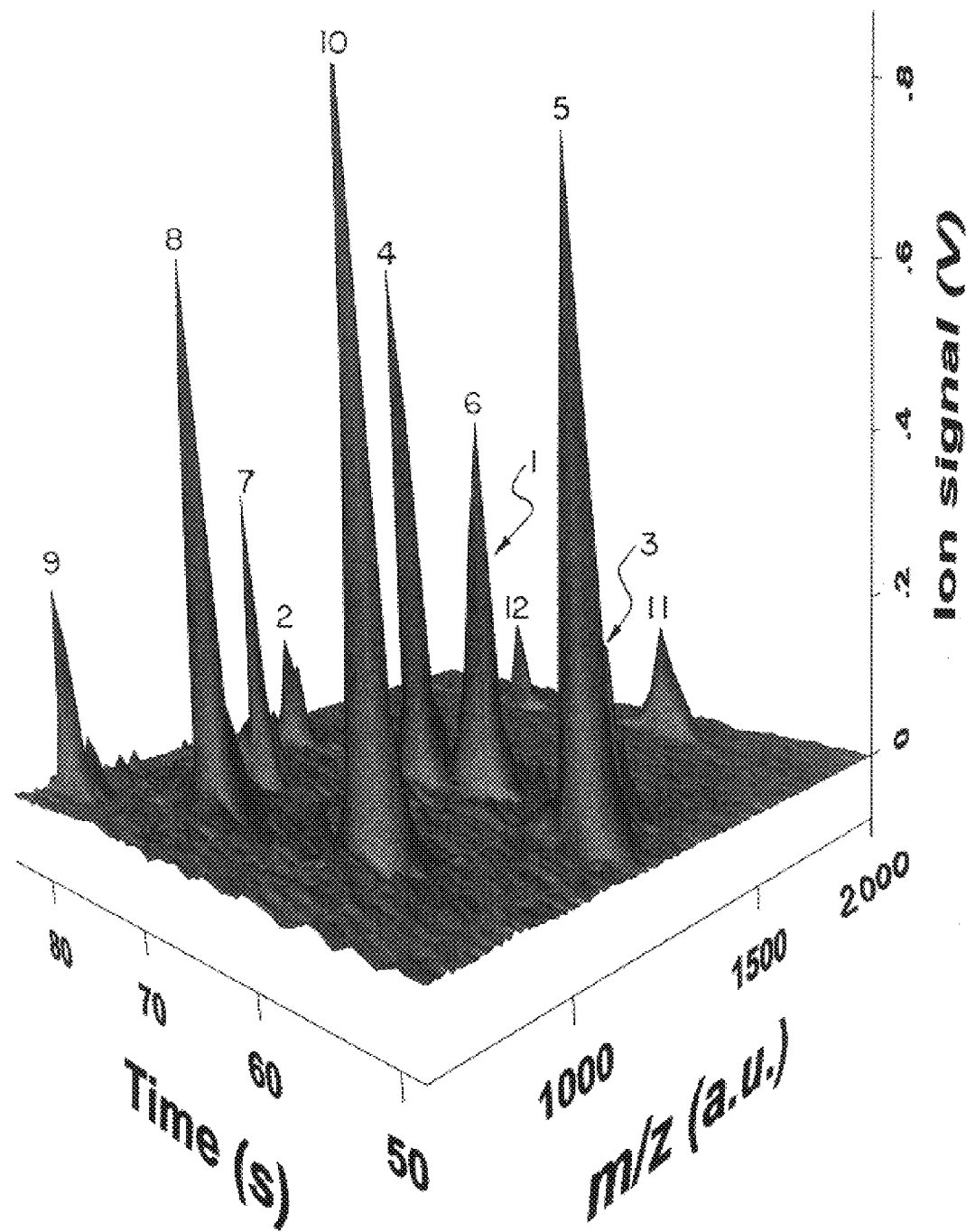
FIG. 12 is a 2-dimensional MALDI-MS electropherogram of angiotensin mixture (see Table 2)

The capillary and the anodic reservoir were filled with 10 mM citric acid solution and the cathodic reservoir in the liquid junction with 10 mM αCHCA solution in 50% (v/v) methanol. Angiotensins were injected by electromigration at 50V/cm within 5 s from a 8.3 μg/mL (each) aqueous peptide mixed solution in the same quantities as in CE-UV. The stepper motor ran at 0.33 rpm and the laser repetition rate was adjusted to 20 Hz, i.e., 2 shots per segment. As shown in FIG. 12, all twelve peptides were resolved and identified on the 2D MS-electropherogram. Since the timing of the experiment was carried out manually, the migration time in CE-MALDI-MS was normalized to the peak 5 in CE-UV (migration time of 52.5 s). This normalized time does not include the period needed for sample transport from the liquid junction to the desorption region (approximately 100 s). Temporal halfwidth of CE-MALDI-MS peaks was lower than those detected by UV, which means that broadening caused by the liquid junction, laminar flow, adsorption in the infusion capillary and deposition process is lower than the broadening caused by finite size of light beamwaist in the commercial UV detector.

EXAMPLE VI

Multiplex Analysis of Samples

Figure 13A:
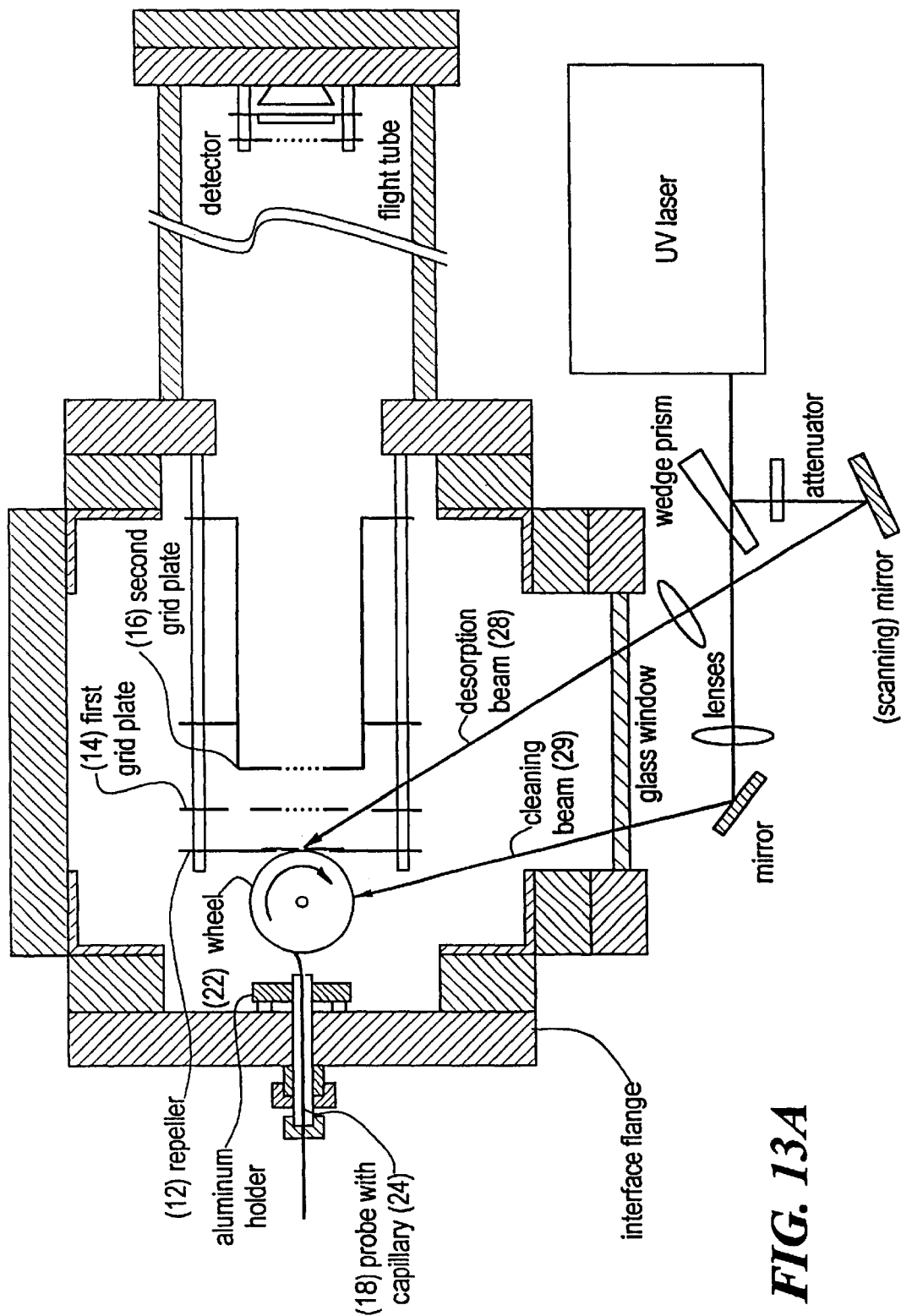
FIG. 13A is a plan view showing another embodiment of an on-line MALDI-TOF MS instrument for practicing a the method of the invention. The rotation wheel sample receptor is oriented at 90° to the orientation of the wheel sample receptor of the embodiment of FIG. 1A so that a cleaning beam 29 can access the wheel in addition to desorption beam 28.
Figure 13B:
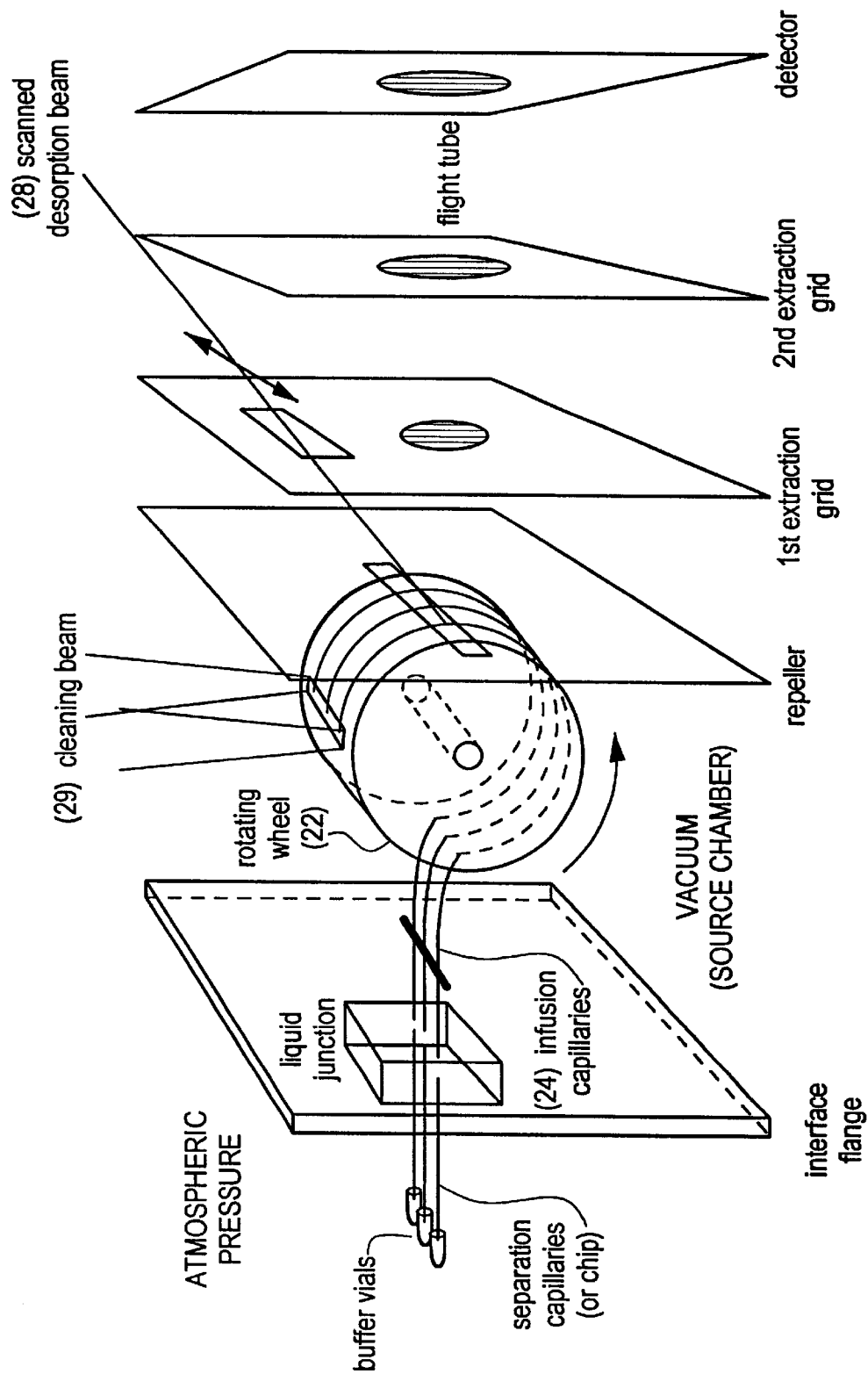
FIG. 13B is a bottom perspective view of the mass spectrometer of FIG. 13A showing multiple multiplexed infusion capillaries simultaneously depositing samples on the rotating wheel.

A sampling device such as a capillary array or microchip having several sample channels can be used for simultaneous introduction and high throughput analysis of multiple samples. As can be seen in FIG. 13B, an array of capillaries 24 is used for simultaneous deposition of multiple samples on rotating wheel 22. Here, the beam of the desorption laser 28 is scanned in steps across the wheel to irradiate every sample sequentially. This approach can take full advantage of the high speed of a time-of-flight mass spectrometer and use the high repetition rate of the desorption laser more efficiently than other configurations.

It is also useful to have automated cleaning and removal of any sample remaining following the desorption step. A cleaning beam 29 can be provided, at a different orientation from that of the desorption laser, to accomplish this purpose. The cleaning beam can be an entirely separate laser from the desorption laser. Alternatively, as can be seen in FIG. 13A, a single laser beam can be split to perform both functions. As only about 5% of the energy of the nitrogen laser beam used in these examples is needed for desorption, the remaining energy of the beam can be used for the cleaning function. Cleaning can also be accomplished mechanically or through the use of heat.

B. Off-Line Sample Preparation

Figure 14:
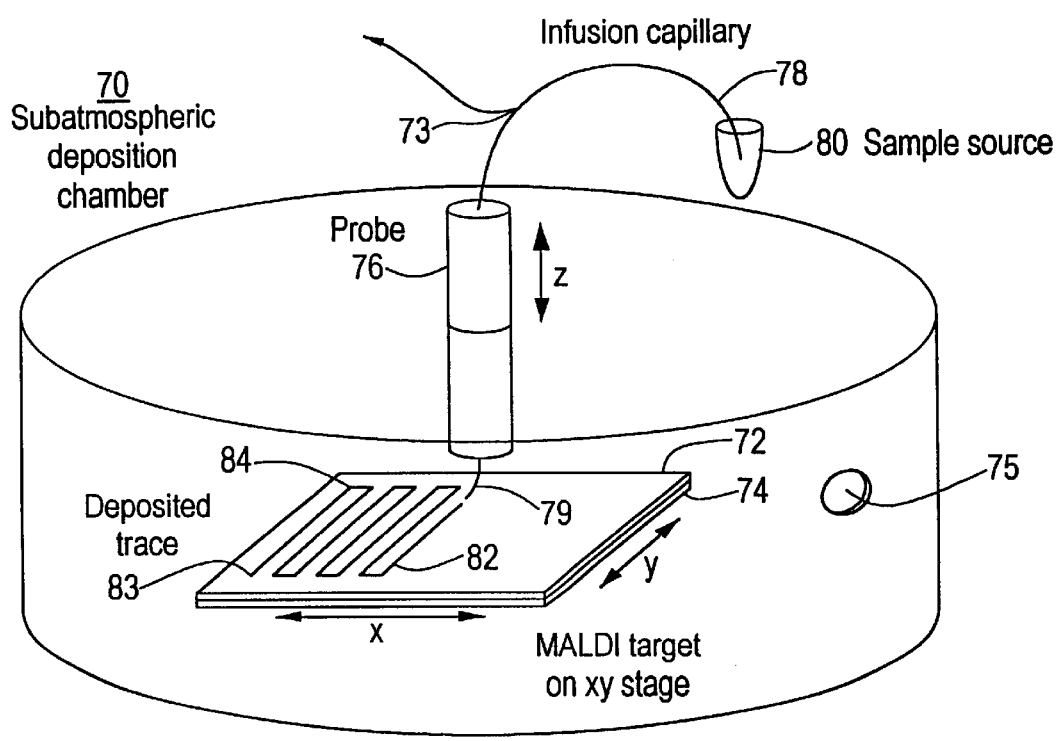
FIG. 14 is a perspective view showing an embodiment of an off-line sample deposition system for practicing a method of the invention.

The sample deposition method of the invention is also amenable to off-line implementation. Referring to FIG. 14, a subatmospheric sample deposition chamber 70 for practicing the method of the invention includes a supported sample receptor 72, such as a typical target plate for use in commercial MALDI-MS instruments, resting on a moving x-y stage 74, and an interface probe 76 for supporting a micro-scale infusion device such as an infusion capillary 78, typically fused silica, which is used to transport an aliquot of a sample from a sample source 80, external to the sample deposition chamber, to the surface of the sample receptor. A sample may be provided as output from a separation or analytical process, e.g., capillary electrophoresis, capillary electrochromatography, capillary isoelectric focusing, capillary isotachophoresis or liquid chromatography. The flow from such a sample may be split, e.g., at T-splitter 73, with only a portion being directed to the sample deposition chamber. The sample receptor itself can be planar, as described, but other configurations are contemplated, such as a rotating drum, disk or tape, with e.g., a metal or plastic thin film overlay, which can be removed and used on a support in the source chamber of a mass spectrometer.

As shown in FIG. 14, probe 76 is movable in the z dimension and can be raised and lowered relative to the receptor surface. Alternatively, the probe can be fixed and supporting stage 74 can additionally be moved in the z dimension. The sample deposition chamber 70 is attached to an evacuation pump through an outlet 75 in the side of the chamber.

In a preferred embodiment of the method of the invention, sample deposition chamber 70 is evacuated to a pressure of approximately 1 Torr or less, which represents a rough vacuum. (Lower chamber pressures may be used but are not necessary.) The pressure differential between the vacuum inside the chamber and atmospheric pressure outside the chamber causes sample liquid to flow through infusion capillary 78, supported by probe 76. A liquid sample, emerging from tip 79 of infusion capillary 78 is deposited under vacuum directly onto moving sample receptor 72 in any pattern desired, e.g., continuous trace or series of dots.

Sample streaks can also be laid down in preformed groves on sample receptor 72. The analyte in the liquid sample can be premixed with a suitable matrix, if desired, e.g., if the sample is to be analyzed by MALDI-MS.

Typically, capillary 78 has a 20 $\mu$m i.d. (150 $\mu$m o.d.), which results in a sample flow rate of ~200 nl/min. At this flow rate, the sample immediately dries or freezes on the sample receptor, forming a continuous trace 82 ~40–60 $\mu$m wide and only few hundred nanometers thick. The flow rate, in general, is controlled by the length and inside diameter of the infusion capillary, the extent of the vacuum and the nature of the solvent.

As shown in FIG. 14, in one embodiment a sample trace 82 from a single capillary can be laid down in a continuous line across the entire surface of the sample receptor. For example, the sample trace pattern shown in FIG. 14 was created by starting at position 83, laying down the first portion of the trace in the +y direction as far as point 84, rotating capillary tip 79 90 degrees and moving a short distance in the +x direction while laying down a connecting portion of the trace, rotating capillary tip 79 again 90 degrees and then laying down the next portion of the trace in the −y direction. Sample deposition can continue in this manner until a sufficient quantity of sample material is deposited on the sample receptor for the intended use. Alternatively, sample traces can be laid down as a series of parallel lines, e.g., while the receptor stage is moving in the +y direction. Probe holder 76 is raised (or sample receptor 72 lowered) while the sample receptor is translated in the +x direction between the laying down of each y dimension trace. Liquid sample may be deposited as a series of droplets, e.g., in a line or other pattern.

As described earlier for the on-line system of the invention and as shown in FIG. 2A, for continuous trace deposition, an infusion capillary is generally bent at the tip, to ensure good liquid contact between the capillary tip and the receptor surface. A slight pressure can be maintained between the tip and the surface, or the tip can be raised slightly and liquid contact only can be maintained between the capillary and the receptor surface. Furthermore, as can be seen in the detailed portion of FIG. 2A and in FIGS. 2B and 2C, the tip of an infusion capillary preferably is tapered to prevent accumulation of deposited solution on the outer capillary wall and clogging of the capillary. Formation of too large a droplet would also mean increased dead volume and resultant band broadening. The liquid sample can detach from the tip, e.g., by surface action or by vibration of the capillary.

Referring again to FIGS. 2B and 2C, it has been found that the width of the deposited trace is roughly proportional to the o.d. of the capillary tip. For example, as can be seen in FIG. 2C, the width of a sample trace deposited with a tapered capillary (20 $\mu$m i.d., 150 $\mu$m o.d., 40–60 $\mu$m tip o.d.) is 40–60 $\mu$m, compared to an approximately 200 $\mu$m wide sample trace deposited from the same capillary that had been perpendicularly cut (FIG. 2B). If a supply of energy is desirable for rapid evaporation and/or sublimation of the solvent, or to prevent solvent in the capillary tip from freezing, it can be provided through the use of a heating element, which can be positioned, e.g., in the supporting stage, on the capillary tip itself or in close proximity thereto.

Figure 15:
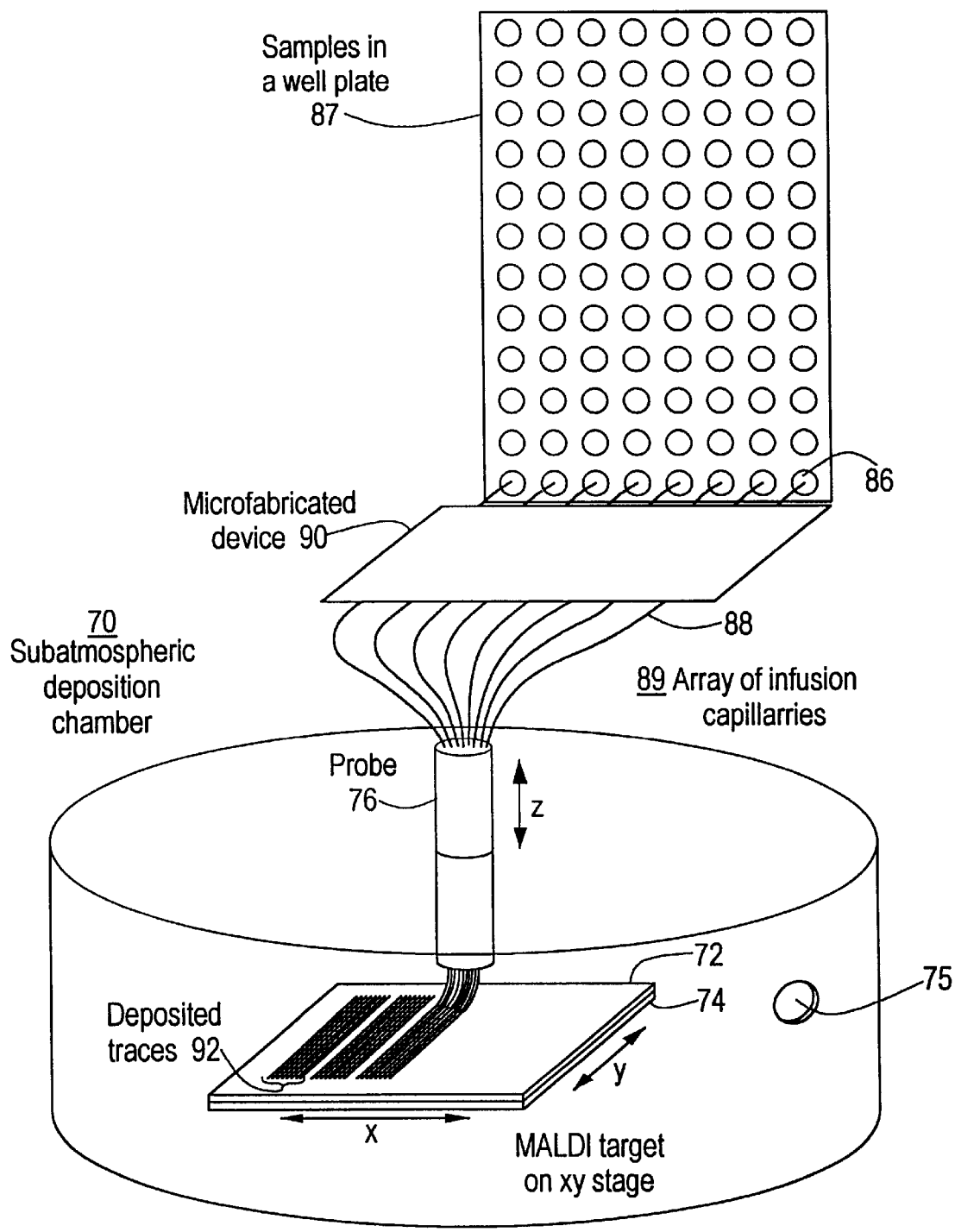
FIG. 15 is a perspective view showing multiple multiplexed infusion capillaries simultaneously depositing samples in an off-line sample deposition system.

The sample deposition method of the invention can also be used with a capillary array or a microfabricated device, such as a microchip, having numerous sample channels. As shown in FIG. 15, samples are drawn from individual wells 86 in a typical 96-well plate 87, by the pressure differential between the outside and the inside of the deposition chamber, through individual capillaries 88 in capillary array 89. In the embodiment shown, the samples are first passed through the channels of microfabricated device 90, where additional sample processing may take place, and are simultaneously deposited inside the sample deposition chamber in parallel traces on moving sample receptor 72. Following the laying down of one set of parallel traces, the sample receptor may be translated in the x dimension, and another set of y dimension parallel traces laid down if desired.

The samples produced by the off-line sample deposition method of the invention are of a unique quality. As described earlier and illustrated in the scanning electron micrographs of deposited samples, FIGS. 3A–3C, the methods of the invention produce homogeneous samples of uniform morphology, e.g., as amorphous or crystalline sample traces or spots. Such samples are suitable for further processing by any desirable method. For example, if MALDI-MS processing is desired, the sample liquid would be premixed with a suitable matrix before sample deposition, and the sample receptor containing the dried sample would be transferred to the source chamber of a mass spectrometer. Other uses for samples prepared by this method can be found, e.g., in the fields of electrochemistry, immunochemistry or optical spectrometry. For example, a fluorescently labeled antibody can be sprayed over the surface of the sample on the receptor and the analytes of interest revealed by laser induced fluorescence detection.

Other Embodiments

The mass spectrometer described herein was a time-of-flight mass spectrometer. This configuration is simple, very fast and particularly efficient in that it uses most of the desorbed ions to record the entire mass spectrum. Other mass spectrometers, such as a Fourier transform ion cyclotron resonance mass spectrometer, a quadruple mass spectrometer or an ion trap mass spectrometer can also be used. Furthermore, tandem systems, such as a quadrupole filter/TOF MS system, are particularly useful. The method of the invention also enables the use of other mass spectrometry techniques, such as MS—MS, which is particularly important for analysis of proteins.

The particular advantages of the on-line method of the invention are on-line coupling, very short analysis time, high MS throughput for a single sample, further increase of throughput by multiplexing (the simultaneous analysis of several samples), high sensitivity and compatibility with existing time-of-flight focusing techniques. The potential of the technique can be usefully exploited, e.g., for sensitive analysis, trace analysis, analysis of both small and large molecules, DNA sequencing, mutation analysis, screening and on-stream analysis.

The off-line method of sample deposition according to the invention has the additional advantage of being useful for the preparation of samples for existing commercial mass spectrometers as it does not require modification to the instrument to be effective. In addition, high quality samples can be prepared for a wide variety of other uses, as described herein.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

REFERENCES

1. Wilm, M.; Mann, M., *Anal. Chem.* 1996, 68, 1–8.
2. Karas, M., Bachmann, D., Bahr., U. and Hillenkamp, F. Int. *J. Mass Spectrom. Ion Processes* 1987, 78, 53–68.
3. Fenn, J. B.; Rosell, J.; Meng, C. K., *J. Am. Soc. Mass Spectrom.* 1997, 8, 1147–1157.
4. Balogh, M. P., *LC GC* 1998, 16, 135.
5. Perera, I. K., Perkins, J. and Kantartzoglou, S. *Rapid. Commun. Mass Spectrom.* 1995, 9, 180–187.
6. Strupat, K., Karas, M. and Hillenkamp, F. *Int. J. Mass Spectrom. Ion Processes* 1991, 111, 89–102.
7. Jespersen, S., Niessen, W. M. A., Tjaden, U. R., van der Greef, J., Litborn, E., Lindberg, U. and Roeraade, J. *Rapid. Commun. Mass Spectrom.* 1994, 8, 581–584.
8. Little, D. P., Cornish, T. J., O'Donnell, M. J., Braun, A., Cotter, R. J. and Koster, H. *Anal. Chem.* 1997, 69, 4540–4546.
9. Stevenson, T. I.; Loo, J. A, *LC GC.* 1998, 16, 54.
10. Zhang, H. Y.; Caprioli, R. M., J. Mass Spectrom. 1996, 31, 1039–1046.
11. Walker, K. L.; Chiu, R. W.; Monnig, C. A.; Wilkins, C. L., *Anal. Chem.* 1995, 67, 4197–4204.
12. Bergman, A. C.; Bergman, T., *J. of Protein Chem.* 1997, 16, 421–423.
13. He, L., Wei, G. and Murray, K. K. *J. Am. Soc. Mass Spectrom.* 1997, 8, 140–147.
14. Fei, X., Wei, G. and Murray, K. K. *Anal. Chem.* 1996, 68, 1143–1147.
15. Russel, D. H. and Beeson, M. D. *J. Mass Spectrom.* 1996, 31, 295–302.
16. Beeson, M. D., Murray, K. K. and Russell, D. H. *Anal. Chem.* 1995, 67, 1981–1986.
17. Murray, K. K., Lewis, T. M., Beeson, M. D. and Russell, D. H. *Anal. Chem.* 1994, 66, 1601–1609.
18. Murray, K. K. and Russell, D. H. *J. Am. Soc. Mass. Spectrom.* 1994, 5, 1–9.
19. Murray, K. K. and Russell, D. H. *Anal. Chem.* 1993, 65, 2534–2537.
20. Nichols, W.; Zweigenbaum, J.; Garcia, F.; Johansson, M.; Henion, J., *LC-GC* 1992, 10, 676–686.
21. Nagra, D. and Li, L. J. Chromatogr. 1995, 711, 235–245.
22. Li, L., Wang, A. P. L. and Coulson, L. D. *Anal. Chem.* 1993, 65, 493–495.
23. He, L., Li, L. and Lubman, D. M. *Anal. Chem.* 1995, 67, 4127–4132.
24. Lustig, D. A. and Lubman, D. M. *Rev. Sci. Instrum.* 1991, 62, 957–962.
25. Dale, M. J., and Knochenmuss, R. and Zenobi, R. *Anal. Chem.* 1996, 68, 3321–3329.
26. Zumbuhl, S.; Knochenmuss, R.; Wulfert, S.; Dubois, F.; Dale, M. J.; Zenobi, R., *Anal. Chem.* 1998, 70, 707–715.
27. Sunner, J.; Dratz, E.; Chen, Y. C., *Anal. Chem.* 1995, 67, 4335–4342.
28. Nelson, R. W., Thomas, R. M. and Williams P. *Rapid. Commun. Mass Spectrom.* 1990, 4, 348–351.
29. Overberg, A., Karas, M., Bahr, U., Kaufmann, R. and Hillenkamp, F. *Rapid Commun. Mass Spectrom.* 1990, 4, 293–296.
30. Zhao, S., Somayajula, K. V., Sharkey, A. G., Hercules, D. M. Fresenius *J. Anal. Chem.* 1990, 338, 588–592.
31 Strobel, F. H., Solouki, M. A., White, M. A. and Russell, D. H. *J. Am. Soc. Mass Spectrom.* 1991, 2, 91.
32. Zhao, S., Somayajula, K. V., Sharkey, A. G., Hercules, D. M., Hillenkamp, F., Karas, M. and Ingendoh, A. *Anal. Chem.* 1991, 63, 450–453.
33. Overberg, A., Karas, M. and Hillenkamp, F. *Rapid. Commun. Mass Spectrom.* 1991, 5, 128–131.
34. Chan, T. W. D., Colburn, A. W. and Derrick, P. J. Org. Mass Spectrom. 1992, 27, 53–56.
35. Cornett, D. S., Duncan, M. A. and Amster, I. J. *Org. Mass Spectrom.* 1992, 27, 831–832.
36. Cornett, D. S., Duncan, M. A. and Amster, I. J. *Anal. Chem.* 1993, 65, 2608–2613.
37. Kim, Y. L., Zhao, S., Sharkey, A. G. and Hercules, D. M. Mikrochim. Acta 1994, 113, 101–111.
38. Perera, I. K., kantartzoglou, S., Dyer, P. E. *Int. J. Mass Spectrom. Ion Processes* 1994, 137, 151.
39. Williams, J. B., Gusev, A. I. and Hercules, D. M. *Macromolecules* 1996, 29, 8114–8150.
40. Zöllner, P., Schmid, E. R. and Allmaier, G. *Rapid. Commun. Mass Spectrom.* 1996, 10, 1278–1282.
41. Chang, S. Y. and Yeung, E. S. *Anal. Chem.* 1997, 69, 2251–2257.
42. Sheehan, E. W. and Willoughby, R. C. *In Proceedings of The 15th ASMS Conference on Mass Spectrometry and Allied Topics*, Palm Springs, Calif., Jun. 1–5, 1997, 115.
43. Dohmeier, D. M., *Thesis*, University of North Carolina, Chapel Hill, 1995.
44. GameroCastano, M.; AguirreDeCarcer, I.; dejuan, L.; delaMora, J. F., *J. Appl. Phys.* 1998, 83, 2428–2434.
45. U.S. Pat. No. 4,055,987.
46. Wiley, W. C. and McLaren, I. H. *Rev. Sci. Instrum.* 1955, 26, 1150.
47. W. Goetzinger and B. L. Karger, PCT Int. Appl. WO9623220 August 1996
48. Lee, E. D.; Muck, W.; Henion, J. D.; Covey, T. R., *Biomed. & Environ. MS* 1989, 18, 844–850.
49. Foret, F., Kirby, D., Karger, B. L., *In Proceedings of the 44th ASMS Conference on Mass Spectrometry and Allied Topics*, Portland, Oreg., May 12–16, 1996, poster # WPH 147.
50. Karas, M. and Hillenkamp, F. *Anal. Chem.* 1988, 60, 2299.
51. Beavis, R. C. and Chait, B. T. *Rapid. Commun. Mass Spectrom.* 1989, 3, 432–435.
52. Xiang., F. and Beavis, R. C. *Org. Mass Spectrom.* 1993, 28, 1424–1429.
53. Xiang., F. and Beavis, R. C. *Rapid. Commun. Mass Spectrom.* 1994, 8, 199–204.
54. Vorm, O., Roepstorff and Mann, M. *Anal. Chem.* 1994, 66, 3218–3287.
55. Vorm, O. and Mann, M. *J. Am. Soc. Mass Spectrom.* 1994, 5, 955–958.
56. Chan, T-W. D., Colburn, A. W., Derrick, P., Gardiner, D. J. and Bowden, M. *Org. Mass Spectrom.* 1992, 27, 188–194.
57. Gusev, A., Wilkinson, W. R., Proctor, A. and Hercules, D. M. *Anal. Chem.* 1995, 67, 1034–1041.
58. Weinberger, S. R., Boernsen, K. O., Finchy, J. W. Robertson, V. and Musselman, B. D. *In Proceedings of the 41st ASMS Conference on Mass Spectrometry and Allied Topics*, San Francisco, Calif., May 31–Jun. 4, 1993, 775a–b.
59. Hutchens, T. W. and Yip, T. T. *Rapid. Commun. Mass Spectrom.* 1993, 7, 576.
60. Mock, K., Sutton, C. W. and Cottrell, J. S. *Rapid. Commun. Mass Spectrom.* 1992, 6, 233–238.
61. Worrall, T. A., Cotter, R. J. and Woods, A. S. *Anal. Chem.* 1998, 70, 750–756.
62. Allmaier, G. *Rapid. Commun. Mass Spectrom.* 1997, 11, 1576–1569.
63. Amado, F. M. L., Dominiques, P., Santana-Marques, M. G., Ferrer-Correia, A. J. and Tomer, K. B. *Rapid. Commun. Mass Spectrom.* 1997, 11, 1347–1352.

64. Dai, Y., Whittal, M. and Li, L. *Anal. Chem.* 1996, 68, 2494–2500.
65. Beavis, R. C. and Chait, B. T. *Rapid. Commun. Mass Spectrom.* 1989, 3, 233.
66. Hillenkamp, F., Karas, M., Beavis, R. and Chait, B. T. *Anal. Chem.* 1991, 63, 1193A –1203A.
67. Koster, K., Lindner, J., Kinsel, G. K. and Grotemeyer, J. *Lect. Notes Phys.* 1991, 389, 139.
68. Karas, M., Bahr, U. and Hillenkamp, F. *Int. J. Mass Spectrom. Ion Processes* 1989, 92, 231.
69. Pospichal, J., Gebauer, P. and Bocek, P. *Chem. Reviews* 1989, 89, 424.

What is claimed is:

1. A method of preparing a sample for analysis, said method comprising the steps of:

providing a liquid sample;

introducing said sample through a micro-scale infusion device into a deposition chamber, said deposition chamber comprising a sample receptor, said deposition chamber, further, being maintained at subatmospheric pressure ; and depositing said sample directly from said infusion device onto a surface of said sample receptor in said chamber.

2. The method of claim 1, further comprising placing said sample receptor comprising said deposited sample into the source chamber of a mass spectrometer.

3. The method of claim 1, wherein, during said depositing step, said infusion device touches said surface of said sample receptor.

4. The method of claim 1, wherein, during said depositing step, liquid contact is maintained between said infusion device and said surface of said sample receptor.

5. The method of claim 1, wherein, in said introducing step, said infusion device is an infusion capillary.

6. The method of claim 5, wherein said infusion capillary transfers said sample from a microfabricated device into said deposition chamber.

7. The method of claim 6, wherein a portion of said transferred sample is diverted prior to transfer of the remaining said sample into said deposition chamber.

8. The method of claim 5, wherein said infusion capillary ends in a tapered tip.

9. The method of claim 1, wherein said liquid sample comprises matrix molecules for matrix assisted laser desorption ionization.

10. The method of claim 9, wherein said matrix molecules are solid.

11. The method of claim 9, wherein said matrix molecules are liquid.

12. The method of claim 1, wherein said sample receptor is selected from the group consisting of a plate, a disk and a tape.

13. The method of claim 1, wherein said sample receptor is movable relative to said infusion device and said relative movement of said receptor is programmable to a particular pattern.

14. The method of claim 1, wherein multiple provided liquid samples are introduced simultaneously into said deposition chamber and said samples are deposited individually and simultaneously directly onto a surface of said sample receptor.

15. The method of claim 14, wherein said multiple liquid samples are introduced into said deposition chamber by means of a capillary array.

16. The method of claim 14, wherein said multiple liquid samples are introduced into said deposition chamber by means of sample channels in a microfabricated device.

17. The method of claim 1, wherein said liquid sample is provided as output from a capillary electrophoresis device, a capillary electrochromatographic device, a capillary isoelectric focusing device or a capillary isotachophoresis device.

18. The method of claim 1, wherein said liquid sample is provided as output from a liquid chromatographic device.

19. A method of high throughput preparation of multiple samples for analysis, said method comprising the steps of:

providing multiple liquid samples;

introducing said multiple samples simultaneously, through a multiple channeled micro-scale infusion device into a deposition chamber, said deposition chamber comprising a sample receptor, said deposition chamber, further, being maintained at subatmospheric pressure; and simultaneously depositing said multiple samples directly from said multiple channeled infusion device onto a surface of said sample receptor, individual samples from said multiple samples being deposited individually.

20. The method of claim 19, wherein multiple infusion capillaries are supported in said multiple channeled infusion device and wherein further said multiple capillaries are positioned so as to deposit said multiple samples directly onto said receptor surface.

21. A deposition chamber for use in preparing a sample for analysis, said chamber comprising;

a deposition chamber capable of holding a vacuum;

a micro-scale infusion device, said infusion device having an entrance end and an exit end;

an interface probe at an orifice in a surface of said deposition chamber, said interface probe positioning said infusion device so that the entrance end of said device is outside said deposition chamber and the exit end of said device is inside said deposition chamber; and a movable sample receptor, said sample receptor being supported in a receptor holder inside said deposition chamber, wherein the exit end of said infusion device is positioned, in relationship to a surface of said movable sample receptor, so as to deposit a sample being introduced into said deposition chamber directly onto a surface of said receptor without breaking a inside said deposition chamber.

22. The deposition chamber of claim 21 wherein said infusion device is an infusion capillary.

23. The deposition chamber of claim 22 wherein said infusion capillary ends in a tapered tip.

24. The deposition chamber of claim 22, wherein said infusion capillary is supported in a capillary holder.

25. A deposition chamber for use in preparing a sample for analysis, said chamber comprising:

a deposition chamber capable of holding a vacuum;

a multiple channeled micro-scale infusion device, wherein channels in said infusion device have entrance ends and exit ends;

an interface probe at an orifice in a surface of said deposition chamber, said interface probe positioning said infusion device so that the entrance ends of said device are outside said deposition chanter and the exit ends of said device are inside said deposition chamber; and a movable sample receptor, said sample receptor being supported in a receptor holder inside said deposition chamber, wherein the exit ends of the channels of said multiple channeled infusion device are positioned, in relationship to a surface of said movable sample receptor, so as to deposit simultaneously multiple samples being introduced into said deposition chamber directly onto a surface of said receptor without breaking a vacuum inside said deposition chamber.

26. The deposition chamber of claim 25 wherein the exit ends of the channels of said multiple channeled infusion device are tapered.

27. The deposition chamber of claim 21 or claim 25, wherein said sample receptor is selected from the group consisting of a plate, a disk and tape.

* * * * *

UNITED STATES PATENT AND TRADEMARK OFFICE
CERTIFICATE OF CORRECTION

PATENT NO. : 6,674,070 B2
DATED : January 6, 2004
INVENTOR(S) : Barry L. Karger et al.

It is certified that error appears in the above-identified patent and that said Letters Patent is hereby corrected as shown below:

Column 3,
Line 54, "1uM" should read -- 1μM --;
Line 55, "ACHCA" should read -- αCHCA --;

Column 4,
Line 2, "ACHCA" should read -- αCHCA --;
Line 9, "1pM" should read -- 1μM --;

Column 6,
Line 3, "mpa.s" should read -- mPa.s --;
Line 46, "ACHCA" should read -- αCHCA --;

Column 11,
Line 19, "CZE1000OR/" should read -- CZE1000R/ --;

Column 13,
Line 13, "pm." should read -- μm. --;

Column 14,
Line 36, "a-cyano-4-hydroxycinnamic" should read -- α-cyano-4-hydroxycinnamic --;
Line 44, "ACHCA" should read -- αCHCA --;

Column 24,
Line 46, "a inside said" should read -- a vacuum inside said --.

Signed and Sealed this

Nineteenth Day of October, 2004

JON W. DUDAS
*Director of the United States Patent and Trademark Office*